(12) United States Patent
Brewer et al.

(10) Patent No.: US 9,834,815 B2
(45) Date of Patent: Dec. 5, 2017

(54) DISCRIMINATORY POSITIVE/EXTRACTION CONTROL DNA

(75) Inventors: Michael Brewer, Boulder, CO (US); Olga Petrauskene, San Carlos, CA (US); Jen-Kuei Liu, Palo Alto, CA (US); Craig Cummings, Pacifica, CA (US); Sueh-Ning Liew, Union City, CA (US)

(73) Assignee: Life Technologies Corporation, Carlsbad, CA (US)

( * ) Notice: Subject to any disclaimer, the term of this patent is extended or adjusted under 35 U.S.C. 154(b) by 677 days.

(21) Appl. No.: 12/731,806

(22) Filed: Mar. 25, 2010

(65) Prior Publication Data

US 2010/0273143 A1    Oct. 28, 2010

Related U.S. Application Data

(60) Provisional application No. 61/163,419, filed on Mar. 25, 2009.

(51) Int. Cl.
*C12Q 1/68* (2006.01)
*C12Q 1/70* (2006.01)

(52) U.S. Cl.
CPC .................................. *C12Q 1/6851* (2013.01)

(58) Field of Classification Search
CPC .................................. C12C 1/689; C12C 1/70
See application file for complete search history.

(56) References Cited

U.S. PATENT DOCUMENTS

| | | | | |
|---|---|---|---|---|
| 2006/0088833 | A1* | 4/2006 | Bange et al. | 435/6 |
| 2007/0015139 | A1* | 1/2007 | Gayral et al. | 435/5 |
| 2007/0269822 | A1* | 11/2007 | Cullor et al. | 435/6 |

FOREIGN PATENT DOCUMENTS

| | | |
|---|---|---|
| WO | WO-00/66777 | 11/2000 |
| WO | WO-2004/055205 | 7/2004 |
| WO | WO-2005/003385 | 1/2005 |
| WO | WO-2010/111509 | 9/2010 |

OTHER PUBLICATIONS

Courtney, B. et al., "Development of internal controls for probe-based nucleic acid diagnostic assays", *Analytical Biochemistry*, vol. 270, Jun. 1, 1999, pp. 249-256.
Ke, D. et al., "Development of conventional and real-time PCR assays for the rapid detection of group B *Streptococci*", *Clinical Chemistry*, vol. 46, No. 3, Mar. 1, 2000, pp. 324-331.
Pals, G., "Detection of a single base substitution in single cells by melting peak analysis using dual-color hybridization probes", *Rapid Cycle Real-Time PCR: Methods and Applications,Genetics and Oncology*, Jan. 1, 2002, pp. 77-84.
PCTUS10028693, International Search Report and Written Opinion dated Aug. 10, 2010, 14 pp.
Wellinghausen, N. et al., "Detection of Legionellae in hospital water samples by quantitative real-time LightCycler PCR", *Applied and Environmental Microbiology*, vol. 67, No. 9, Sep. 2001, pp. 3985-3993.
Zimmermann, K. et al., "Technical Aspects of Quantitative Competitive PCR", *Biotechniques*, vol. 21, No. 2, Aug. 1, 1996, p. 268-279.
Ririe, et al., "Product Differentiation By Analysis of DNA Melting Curves During the Polymerase Chain Reaction", *Analytical Biochemistry*, vol. 245, 1997, 154-160.

* cited by examiner

*Primary Examiner* — David Thomas
(74) *Attorney, Agent, or Firm* — Daphne Reddy

(57) ABSTRACT

The present teachings generally relate to methods and kits incorporating a discriminating positive control for determining whether a particular microorganism or group of microorganisms are present in a sample, for example but not limited to a food, environmental, agricultural, biopharmaceutical, pharmaceutical, or water sample. According to certain methods, at least part of a starting material, for example but not limited to, a food, environmental, agricultural, biopharmaceutical, pharmaceutical, or water sample can be combined with a culture medium and incubated under conditions suitable for microbial growth followed by extracting microorganism and added control nucleic acids for analysis. The extracted nucleic acids are amplified and the amplified nucleic acids are detected, directly or indirectly, and the fidelity of the methods and the presence or absence of the corresponding microorganism is determined because the discriminating positive control provides both confirmatory results for the methods used but eliminates false positive results.

22 Claims, 1 Drawing Sheet

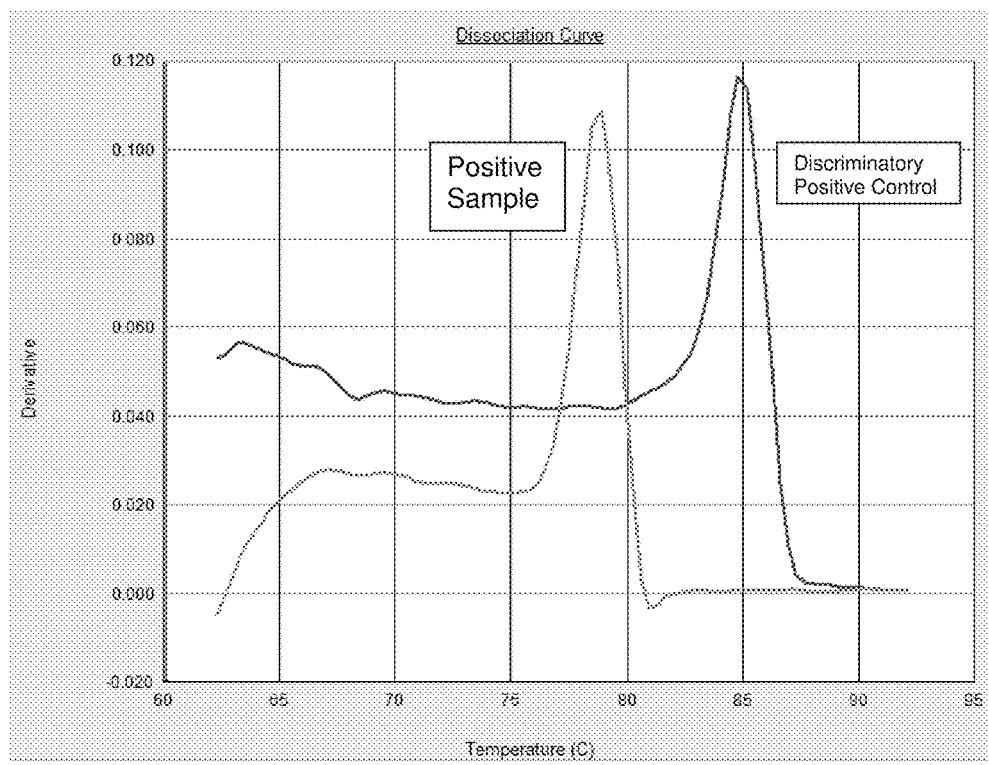

DISCRIMINATORY POSITIVE/EXTRACTION CONTROL DNA

CROSS REFERENCE TO RELATED APPLICATIONS

This application claims the benefit of U.S. Provisional Patent Application No. 61/163,419 filed Mar. 25, 2009, the entire disclosure of which is incorporated herein by reference.

TECHNICAL FIELD

The present teachings generally relate to methods and kits utilizing a discriminatory positive nucleic acid control in the extraction and amplification of test material in assays performed for determining whether a particular microorganism or group of microorganisms are present in a starting material, for example but not limited to a food sample, a water sample, an environmental sample, an agricultural sample, a biopharmaceutical sample, or a pharmaceutical sample.

BACKGROUND

Rapid pathogen detection, contamination and bioburden monitoring, particularly for safety and quality control testing of foods, including beverages and drinking water, agricultural, including GMO-modified foods, environmental, including cell culture media, biopharmaceuticals, including the manufacturing process, and pharmaceuticals, including parenteral drugs, is an ongoing challenge. Microbial contaminants are a major concern in the biopharmaceutical industry and for regulatory organizations, including those charged with public health and safety. Contamination by microorganisms is therefore of significant concern to the biopharmaceutical industry, which is dependent on continuous cell culture for the production of drugs, vaccines, and other "biologics". Likewise, when testing for the bioburden in pharmaceutical manufacturing of biopharmaceuticals, the nucleic acid from non-viable contaminants would still be detectable in an amplification reaction. Conversely, use of actual pathogen nucleic acid controls creates the potential for contamination of test samples and false positive results.

To address these concerns, described herein is a discriminating positive control that confirms nucleic acid extraction, amplification as well as providing differentiation of a true positive in a sample from a false positive due to inadvertent contamination of the test sample with positive control DNA. Further, the discriminating positive control will eliminate or reduce the concern of contamination resulting from supplementing a positive control reaction with nucleic acid derived from the microorganism of interest.

SUMMARY

According to some of the disclosed methods, test sample comprising but not limited to a food sample, a water sample, an environmental sample, an agricultural sample, a biopharmaceutical sample, or a pharmaceutical sample is mixed with a discriminating positive control nucleic acid sequence; extracting nucleic acid from at least some of the test sample mixture; contacting the extracted nucleic acid and the control nucleic acid with a primer, wherein the primer binds to the extracted nucleic acid and the control nucleic acid; amplifying at least some of the extracted nucleic acid and the control nucleic acid; and detecting at least some of the amplified nucleic acids. The test sample having a bacterium or a virus and the primer contacts the nucleic acid of the positive control and the microorganism. In certain embodiments, the amplified nucleic acid comprises discriminatory positive control and microorganism nucleic acids and the detected nucleic acid comprises discriminatory positive control and microorganism nucleic acids, wherein the amplifying comprises a microorganism-specific primer pair and a polymerase chain reaction (PCR). In some embodiments, the microorganism comprises a multiplicity of different microorganisms, the microorganism-specific primer pair comprises a multiplicity of different microorganism-specific primer pairs, and the detecting comprises a multiplicity of different amplified nucleic acids, and further the detecting can comprise a multiplicity of different reporter probes. The detecting comprises a reporter probe are selected from the group consisting of a nucleic acid dye, a reporter probe, or a reporter probe and a nucleic acid dye and the detecting distinguishes an amplicon for the discriminatory positive control from an amplicon for the microorganism, wherein said detecting comprises a melting temperature for the discriminatory positive control distinguishable from a melting temperature for the microorganism or a melt curve for the discriminatory positive control distinguishable from a melt curve for the microorganism, or distinguishing of the amplicons is by sequencing.

In some embodiments, a method for determining the presence of a microorganism comprising, mixing a test sample having at least one microorganism with a discriminating positive control nucleic acid sequence; extracting nucleic acid from at least some of the test sample; contacting the extracted nucleic acid and the control nucleic acid with at least one primer and at least one reporter probe, wherein the at least one primer and the at least one reporter probe binds to the extracted nucleic acid of the at least one microorganism and the control nucleic acid; amplifying at least some of the extracted nucleic acid of the at least one microorganism and the control nucleic acid; and detecting at least some of the amplified nucleic acids, wherein the test sample comprises at least one of a bacterium or a virus including an isolated colony, a loopful of cells, an edge of a filamentous colony, a culture broth, an enriched culture broth, a food sample, an environmental sample, an agricultural sample, a biopharmaceutical sample, a pharmaceutical sample, or water. In some embodiments, the primer contacts the nucleic acid of the positive control and the microorganism and the probe contacts the nucleic acid of the positive control and the microorganism. In further embodiments, the amplified and detected nucleic acid comprises discriminatory positive control and microorganism nucleic acids and the amplification is by a polymerase chain reaction (PCR). In some embodiments, the microorganism comprises a multiplicity of different microorganisms, the microorganism-specific primer pair comprises a multiplicity of different microorganism-specific primer pairs, and the detecting comprises a multiplicity of different amplified nucleic acids and the amplifying further comprises a multiplicity of different reporter probes. The reporter probe is selected from the group consisting of a nuclease probe, an extension probe and a hybridizing probe and the detecting is a fluorescence of at least one probe different from the fluorescence of at least a second probe. In further embodiments the amplifying comprises at least two microorganism-specific primer pairs and a polymerase chain reaction (PCR).

In some embodiments, disclosed is a method for determining the presence of a microorganism comprising, mixing a test sample having at least one microorganism with a discriminating positive control nucleic acid sequence;

extracting nucleic acid from at least some of the test sample; contacting the extracted nucleic acid and the control nucleic acid with at least one primer and at least two reporter probes, wherein the at least one primer binds to both the extracted nucleic acid of the at least one microorganism and to the control nucleic acid, and a first reporter probe of the at least two reporter probes binds to the nucleic acid of the microorganism and a second reporter probe of the at least two reporter probes binds to the control nucleic acid; amplifying at least some of the extracted nucleic acid of the at least one microorganism and the control nucleic acid; and detecting at least some of the amplified nucleic acids.

the In some embodiments, disclosed is a method for determining the presence of a microorganism comprising, taking an aliquot of a test sample; extracting nucleic acid from at least some of the test sample; mixing the extracted nucleic acid with a discriminating positive control nucleic acid sequence; contacting the extracted nucleic acid and the control nucleic acid with a primer, wherein the primer binds to the extracted nucleic acid and the control nucleic acid; amplifying at least some of the extracted nucleic acid and the control nucleic acid; and detecting at least some of the amplified nucleic acids.

Kits for performing certain of the instant methods are also disclosed.

These and other features of the present teachings are set forth herein.

BRIEF DESCRIPTION OF THE DRAWINGS

The skilled artisan will understand that the drawings, described below, are for illustration purposes only. These FIGURES are not intended to limit the scope of the present teachings in any way.

FIG. 1 schematically depicts certain embodiments of the current teachings. Those in the art will understand that discriminating between a true positive in a test sample and a discriminatory positive control by differences in melt curve temperature depends in part on: (1) the $T_m$ of the discriminating positive control amplicon, and (2) the $T_m$ of the amplicon of the microorganism of interest.

DETAILED DESCRIPTION

It is to be understood that both the foregoing general description and the following detailed description are exemplary and explanatory only and are not intended to limit the scope of the current teachings. In this application, the use of the singular includes the plural unless specifically stated otherwise, although terms such as at least one or at least some of are sometimes used for illustration purposes, among other things. For example but without limitation, "a microorganism" means that more than one microorganism, including one or more microorganism of the same microbial species, as well as two or more different species of microorganism, e.g., three different species of bacteria, a bacterial species and a fungal species, a bacterial species and an archaeal species, a fungal species and a particular virus, and so forth as well as nucleic acid from a cell, a cell culture and a culture of cells. Also, the use of "comprise", "contain", and "include", or modifications of those root words, for example but not limited to, "comprises", "contained", and "including", are not intended to be limiting.

The section headings used herein are for organizational purposes only and are not to be construed as limiting the described subject matter in any way. All literature cited in this specification, including but not limited to, patents, patent applications, articles, books, and treatises are expressly incorporated by reference in their entirety for any purpose. In the event that any of the incorporated literature contradicts any term defined herein, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The present teachings provide methods and kits for determining the presence or absence of a given microorganism in a sample, for example but not limited to, a pathogen in a food sample, cultured cells, including but not limited to stem cells, CHO, Vero, HeLa, cultured animal cells, and so on, an agricultural, environmental, or biopharmaceutical sample including but not limited to the research, development, manufacturing and quality control/quality assurance testing of peritoneal, inhalation and topical pharmaceuticals and tissue therapeutics. Microorganisms can include but are not limited to bacteria, virus, mycoplasma, and nucleic acids extracted from the aforementioned samples.

In one embodiment, microorganisms from the entire volume of an enriched medium or an aliquot of the enriched medium, for example but not limited to a one mL aliquot taken from a 250 mL of enriched medium are concentrated and processed. In some instances, typically due to the nature of the starting material or the composition of the medium (for example but not limited to when the enriched medium comprises large fragments of starting material or other particulate matter) it may not be practical to concentrate the microorganisms from the entire volume of enriched medium. In such instances, as much as the enriched medium as is realistically possible is concentrated, typically after allowing the large fragments in the enriched medium to settle to the bottom of the reaction vessel. At least some of the nucleic acid is extracted from concentrated microorganisms and amplified. At least some of the amplification products are detected, directly or indirectly, and the presence or absence of the microorganism in the sample can be determined.

The terms "amplicon" and "amplification product" as used herein generally refers to the product of an amplification reaction. An amplicon can be double-stranded or single-stranded, and can include the separated component strands obtained by denaturing a double-stranded amplification product. In certain embodiments, the amplicon of one amplification cycle can serve as a template in a subsequent amplification cycle.

The terms "annealing" and "hybridizing", including without limitation variations of the root words hybridize and anneal, are used interchangeably and mean the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions may also contribute to duplex stability. Conditions under which primers anneal to complementary or substantially complementary sequences are well known in the art, e.g., as described in Nucleic Acid Hybridization, A Practical Approach, Hames and Higgins, eds., IRL Press, Washington, D.C. (1985) and Wetmur and Davidson, Mol. Biol. 31:349, 1968. In general, whether such annealing takes place is influenced by, among other things, the length of the complementary portion of the primers and their corresponding primer-binding sites in adapter-modified molecules and/or extension products, the pH, the temperature, the presence of mono- and divalent cations, the proportion of G and C nucleotides in the hybridizing region, the viscosity of the medium, and the presence of denaturants. Such variables influence the time required for hybridization. The presence of certain nucleotide analogs or minor groove binders in the complementary portions of the primers and reporter probes can also influence hybridization conditions. Thus, the preferred annealing conditions will depend upon the particular application. Such conditions, however, can be routinely determined by persons of ordinary skill in the art, without undue experimentation. Typically, annealing conditions are selected to allow the disclosed primers to selectively hybridize with a complementary or substantially complementary sequence in their corresponding adapter-modified molecule and/or extension product, but not hybridize to any significant degree to other sequences in the reaction.

The term "selectively hybridize" and variations thereof means that, under appropriate stringency conditions, a given sequence (for example but not limited to a primer) anneals with a second sequence comprising a complementary string of nucleotides (for example but not limited to a target flanking sequence or a primer-binding site of an amplicon), but does not anneal to undesired sequences, such as non-target nucleic acids or other primers. Typically, as the reaction temperature increases toward the melting temperature of a particular double-stranded sequence, the relative amount of selective hybridization generally increases and mis-priming generally decreases. In this specification, a statement that one sequence hybridizes or selectively hybridizes with another sequence encompasses situations where the entirety of both of the sequences hybridize to one another, and situations where only a portion of one or both of the sequences hybridizes to the entire other sequence or to a portion of the other sequence.

The terms "substantially" and "substantially the same" as used herein indicate the substance being so described is largely but not entirely, wholly or completely that which is specified.

In this specification, a statement that one nucleic acid sequence is the same as or substantially the same as another nucleic acid sequence encompasses situations where both of the nucleic acid sequences are completely the same as or substantially the same as the other sequence, and situations where only a portion of one of the sequences is the same as or substantially the same as a portion of the entire other sequence. Likewise, a statement that one nucleic acid sequence is complementary to or substantially complementary to another nucleotide sequence encompasses situations where both of the nucleotide sequences are completely complementary or substantially complementary to one another, and situations where only a portion of one of the sequences is complementary to or substantially complementary to a portion of the entire other sequence. Further, a statement that one nucleic acid sequence primer binding site is the same to or substantially identical to another nucleic acid sequence primer binding site encompasses the situation where both of the primer binding sites are completely the same or substantially the same to one another, and situations where only a portion of one of the sequences is the same to or substantially the same to a portion of the entire other primer binding site.

The term "corresponding" as used herein refers to at least one specific relationship between the elements to which the term relates. For illustration purposes but not as a limitation, at least one forward primer of a particular microbe-specific primer pair corresponds to at least one reverse primer of the same primer pair; at least one primer is designed to anneal with the flanking sequence of the corresponding target region and/or the primer-binding portion of at least one corresponding amplicon; the direct or indirect detection of a particular amplification product indicates the presence of the corresponding microorganism in the sample being evaluated; and so forth.

The terms "denaturing" and "denaturation" as used herein refer to any process in which a double-stranded polynucleotide, including without limitation, a microbial nucleic acid fragment comprising at least one target region, a double-stranded amplicon, or a polynucleotide comprising at least one double-stranded segment, is converted to two single-stranded polynucleotides or to a single-stranded or substantially single-stranded polynucleotide, as appropriate. Denaturing a double-stranded polynucleotide includes without limitation, a variety of thermal and chemical techniques which render a double-stranded nucleic acid or a double-stranded segment of an single nucleic acid single-stranded or substantially single-stranded. Those in the art will appreciate that the denaturing technique employed is generally not limiting unless it substantially interferes with a subsequent annealing or enzymatic step of an amplification reaction or with the detection technique.

The term "double-stranded," as used herein refers to one or two nucleic acid strands that have hybridized along at least a portion of their lengths. Hence, "double-stranded" does not mean that a nucleic acid must be entirely double-stranded. Instead, a double-stranded nucleic acid can have one or more single-stranded segment and one or more double-stranded segment.

As used herein, the term "$T_m$" is used in reference to melting temperature. The melting temperature is the temperature at which a population of double-stranded nucleic acid molecules becomes half dissociated into single strands. The $T_m$ can be altered by changes in the length of the molecule and the composition of the nucleotide sequence. For example, a higher $T_m$ can be associated with a high GC content.

As used herein, the term "melt curve" is used in reference to a graphical presentation of an experimental determination of $T_m$. The determination of $T_m$ is well known to one of ordinary skill in the art. For example, the melt curve can be determined following a polymerase chain reaction by heating the population of double-stranded nucleic acid molecules from approximately 60° C. to approximately 90° C. at 0.1 to 1.0 second intervals, and plotting the derivative of the dissociation of the double-stranded nucleic acid verses temperature. The apex of the peak represents the dissociation of half the double-stranded molecules into single strands.

A "microfluidics device" is a reaction vessel comprising at least one microchannel, generally including an internal dimension of one millimeter or less. Microfluidics devices typically employ very small reaction volumes, often on the order of one or a few microliters (μL), nanoliters, or picoliters. Those in the art will appreciate that the size, shape, and composition of a microfluidics device is generally not a limitation of the current teachings. Rather, any suitable microfluidics devices can be employed in performing one or more steps of the disclosed methods. Descriptions of exemplary microfluidics devices and uses thereof can be found in, among other places, Fiorini and Chiu, BioTechniques 38:429-46 (2005); Kelly and Woolley, Analyt. Chem. 77(5):

96A-102A (2005); Cheuk-Wai Kan et al., Electrophoresis 25:3564-88 (2004); and Yeun et al., Genome Res. 11:405-12 (2001).

The term "minor groove binder" as used herein refers to a small molecule that fits into the minor groove of double-stranded DNA, sometimes in a sequence specific manner. Generally, minor groove binders are long, flat molecules that can adopt a crescent-like shape and thus, fit snugly into the minor groove of a double helix, often displacing water. Minor groove binding molecules typically comprise several aromatic rings connected by bonds with torsional freedom, for example but not limited to, furan, benzene, or pyrrole rings.

As used herein, the term "primer-binding site" refers to a region of a polynucleotide sequence, typically a sequence flanking a target region and/or an amplicon that can serve directly, or by virtue of its complement, as the template upon which a primer can anneal for any suitable primer extension reaction known in the art, for example but not limited to, PCR. It will be appreciated by those of skill in the art that when two primer-binding sites are present on a single polynucleotide, the orientation of the two primer-binding sites is generally different. For example, one primer of a primer pair is complementary to and can hybridize with the first primer-binding site, while the corresponding primer of the primer pair is designed to hybridize with the complement of the second primer-binding site. Stated another way, in some embodiments the first primer-binding site can be in a sense orientation, and the second primer-binding site can be in an antisense orientation. A primer-binding site of an amplicon may, but need not comprise the same sequence as or at least some of the sequence of the target flanking sequence or its complement.

Those in the art understand that as a target region and/or an amplification product is amplified by certain amplification means, the complement of the primer-binding site is synthesized in the complementary amplicon or the complementary strand of the amplicon. Thus, it is to be understood that the complement of a primer-binding site is expressly included within the intended meaning of the term primer-binding site, as used herein.

As used herein, the term "probe-binding site" refers to a region of a polynucleotide sequence, typically a microbial amplicon that can serve directly, or by virtue of its complement, as the template upon which a probe (for example but not limited to a reporter probe) can anneal. In certain embodiments, a tailed primer comprises a probe-binding site or a portion of a probe-binding site. Those in the art understand that as a nucleic acid sequence is amplified by certain amplification means, the complement of the probe-binding site is synthesized in the complementary amplicon or the complementary strand of the amplicon. Thus, it is to be understood that the complement of a probe-binding site is expressly included within the intended meaning of the term probe-binding site, as used herein.

As used herein, the terms "polynucleotide", "oligonucleotide", and "nucleic acid" are used interchangeably and refer to single-stranded and double-stranded polymers of nucleotide monomers, including without limitation 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$, and the like. A polynucleotide may be composed entirely of deoxyribonucleotides, entirely of ribonucleotides, or chimeric mixtures thereof and can include nucleotide analogs. The nucleotide monomer units may comprise any nucleotide or nucleotide analog. Polynucleotides typically range in size from a few monomeric units, e.g. 5-40 when they are sometimes referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytosine, "G" denotes deoxyguanosine, "T" denotes thymidine, and "U" denotes deoxyuridine, unless otherwise noted.

As used herein, the term "reaction vessel" generally refers to any container, chamber, device, or assembly, in which a reaction can occur in accordance with the present teachings. In some embodiments, a reaction vessel can be a microtube, for example but not limited to a 0.2 mL or a 0.5 mL reaction tube such as a MicroAmp® Optical tube (Applied Biosystems) or a micro-centrifuge tube, or other containers of the sort in common practice in molecular biology laboratories. In some embodiments, a reaction vessel comprises a well of a multi-well plate, a spot on a glass slide, or a channel or chamber of a microfluidics device, including without limitation an Applied Biosystems TaqMan® Low Density Array. For example but not as a limitation, a plurality of reaction vessels can reside on the same support. In some embodiments, lab-on-a-chip like devices, available for example from Caliper and Fluidigm, can serve as reaction vessels in the disclosed methods. It will be recognized that a variety of reaction vessels are commercially available or can be designed for use in the context of the present teachings.

The term "reporter group" is used in a broad sense herein and refers to any identifiable or detectable tag, label, or moiety.

The term "antibody" is used in a broad sense, and is intended to include not only intact antibody molecules, for example but not limited to immunoglobulin A, immunoglobulin G and immunoglobulin M, but also any immunoreactive component(s) of an antibody molecule that immunospecifically bind to at least one epitope. Some non-limiting examples of immunoreactive components include FAb fragments, FAb' fragments, FAb'2 fragments, single chain antibody fragments (scFv), miniantibodies, diabodies, crosslinked antibody fragments, Affibody® molecules, and the like. Immunoreactive components derived using antibody engineering or protein engineering techniques are also expressly within the meaning of the term antibody, as used herein. Descriptions of antibody engineering, can be found in, among other places, J. Maynard and G. Georgiou, Ann. Rev. Biomed. Eng. 2:339-76 (2000); Antibody Engineering, R. Kontermann and S. Dübel, eds., Springer Lab Manual, Springer Verlag (2001); A. Worn and A. Plückthun, J. Mol. Biol. 305:989-1010 (2001); J. McCafferty et al., Nature 348:552-54 (1990); Wier et al., FEBS Letter, 432:45-9 (1998); A. Plückthun and P. Pack, Immunotechnology, 3:83-105 (1997); U.S. Pat. No. 5,831,012; and S. Paul, Antibody Engineering Protocols, Humana Press (1995).

The skilled artisan will appreciate that antibody can be obtained from a variety of sources, including but not limited to polyclonal antibody, monoclonal antibody, monospecific antibody, recombinantly expressed antibody, humanized antibody, plantibodies, and the like; and can be obtained from a variety of animal species, including rabbit, mouse, goat, rat, human, horse, bovine, guinea pig, chicken, sheep, donkey, human, and the like. A wide variety of antibody is commercially available and custom-made antibody can be obtained from a number of contract labs. Descriptions of antibodies can be found in, among other places, Current Protocols in Immunology, Coligan et al., eds., John Wiley &

Sons (1999, including updates through September 2005); Basic Methods in Antibody Production and Characterization, G. Howard and D. Bethel, eds., CRC Press (2000); J. Goding, Monoclonal Antibodies: Principles and Practice, 3d Ed., Academic Press (1996); E. Harlow and D. Lane, Using Antibodies, Cold Spring Harbor Lab Press (1999); P. Shepherd and C. Dean, Monoclonal Antibodies: A Practical Approach, Oxford University Press (2000); A. Johnstone and M. Turner, Immunochemistry 1 and 2, Oxford University Press (1997); C. Borrebaeck, Antibody Engineering, 2d ed., Oxford University Press (1995); A. Johnstone and R. Thorpe, Immunochemistry in Practice, Blackwell Science, Ltd. (1996); H. Zola, Monoclonal Antibodies: Preparation and Use of Monoclonal Antibodies and Engineered Antibody Derivatives (Basics: From Background to Bench), Springer Verlag (2000); and S. Hockfield et al., Selected Methods for Antibody and Nucleic Acid Probes, Cold Spring Harbor Lab Press (1993). Additionally, a vast number of antibodies are commercially available, including labeled or unlabeled; polyclonal, monoclonal, and monospecific antibodies, as well as immunoreactive components thereof; custom antibody suppliers, and the like can be found on the World Wide Web at, among other places, the Antibody Search page at biocompare.com, the Antibody Resource Page at antibodyresource.com, and the Antibody Explorer page at sigmaaldrich.com.

The term "chaotrope" as used herein, refers to a substance that causes disorder in a protein or nucleic acid by, for example, but not limited to, altering the secondary, tertiary, or quaternary structure of a protein or a nucleic acid while leaving the primary structure intact. Exemplary chaotropes include, but are not limited to, guanidine hydrochloride (GuHCl), guanidinium thiocyanate (GuSCN), potassium thiocyanate (KSCN), sodium iodide, sodium perchlorate, urea, and the like. A typical anionic chaotropic series, shown in order of decreasing chaotropic strength, includes: $CCl_3COO^- >> CNS^- > CF_3COO^- > ClO_4^- > I^- > CH_3COO^- > Br^-$, $Cl^-$, or $CHO_2^-$. Descriptions of chaotropes and chaotropic salts can be found in, among other places, K. Hamaguchi et al., Proc. Natl. Acad. Sci. 62: 1129-1136, 1962; The Effect Of Electrolytes On The Stability Of The Deoxyribonucleate Helix, J. Amer. Chem. Soc. 84: 1329-1338; U.S. Pat. Application Publication No. US 2002/0177139; and U.S. Pat. No. 5,234,809.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this illustration, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The term "culture medium" as used herein refers to a composition, oftentimes a liquid that is suitable for supporting the growth of a microorganism of interest. A culture medium can be a general- or all-purpose medium, capable of supporting the growth of a variety of different microorganisms. In certain embodiments, the culture media comprises a selective media or an enrichment media. A selective media comprises at least one component that prevents or retards the growth of unwanted microorganisms without inhibiting the growth of the microorganism(s) of interest, for example but not limited to certain dyes, antimicrobials, or salts. An enrichment media comprises at least one component that enhances the growth of the microorganism(s) of interest and it may or may not be designed to inhibit the growth of other microorganisms. Those in the art will appreciate a particular culture media may be selective or inhibitory for the growth of a given microorganism, but that suitable culture media can be identified by consulting the scientific literature or can be determined by routine experimentation. Non-limiting examples of culture media include Brain Heart Infusion (BHI) broth, Fraser broth, and tryptic soy broth. In some embodiments, a culture medium can be solid or semi-solid and can, but need not, include agar.

Certain embodiments of the current teachings include a surfactant such as a detergent or an emulsifying agent, typically for use in extracting nucleic acids. Detergents are frequently used in cell lysis protocols, as they often disrupt cell walls and cell membranes and can solubilize proteins and include without limitation ionic detergents, non-ionic detergents, and zwitterionic detergents. Ionic detergents, including without limitation anionic detergents and cationic detergents, are often used for obtaining nucleic acids. Anionic detergents, for example but not limited to sodium dodecyl sulfate (SDS), are typically effective in solubilizing protein but may precipitate in high salt solutions. Nonionic detergents, such as Triton X, Tween 20, and NP-40, are typically less effective than the ionic detergents at disrupting protein aggregates.

A "cationic detergent" has a positively charged group under the conditions examined. Typically, cationic detergents may contain quaternary amines or tertiary amines. However, at the proper pH, cationic detergents can contain primary or secondary amines. Exemplary quaternary amine detergents include, but are not limited to, cetylpyridinium chloride, cetyl trimethyl ammonium bromide (CTAB; Calbiochem #B22633 or Aldrich #85582-0), cetyl trimethyl ammonium chloride (CTACl; Aldrich #29273-7), dodecyl trimethyl ammonium bromide (Sigma #D-8638), octyl trimethyl ammonium bromide, tetradecyl trimethyl ammonium bromide, octadecyl trimethyl ammonium bromide, stearoalkonium chloride, olealkonium chloride, cetrimonium chloride, alkyl trimethyl ammonium methosulfate, palmitamidopropyl trimethyl chloride, quaternium 84 (Mackernium NLE; McIntyre Group, Ltd.), wheat lipid epoxide (Mackernium WLE; McIntyre Group, Ltd.), and the like. Exemplary ternary amine detergents include, but are not limited to, octyldimethylamine, decyldimethylamine, dodecyldimethylamine, tetradecyldimethylamine, hexadecyldimethylamine, octyldecyldimethylamine, octyldecylmethylamine, didecylmethylamine, dodecylmethylamine, triacetylammonium chloride, cetrimonium chloride, alkyl dimethyl benzyl ammonium chloride, and the like.

According to the current teachings, zwitterionic compounds include zwitterionic detergents, including but not limited to sulfobetaines; and the non-detergent zwitterions, including but not limited to non-detergent sulfobetaines (NDSBs). A "zwitterionic detergent" commonly possesses some properties of ionic detergents and some properties of non-ionic detergents. For example, but not as a limitation, they typically fail to bind ion-exchange resins and lack electrophoretic mobility, like the nonionic detergents; but like ionic detergents, they efficiently disrupt many protein-protein interactions. Under certain conditions, a zwitterionic detergent is capable of simultaneously carrying both positive and negative charges on the same group of atoms or compound, and thus may have a net zero charge. Non-limiting examples of zwitterionic detergents include N,N-bis(3-D-

Gluconamidopropyl)cholamide (BigCHAP), 3-(3-Cholamidopropyl)dimethylammonio]-1-propanesulfonate (CHAPS), 3-[(3-Cholamidopropyl)dimethylammonio]-2-hydroxy-1-propanesulfonate (CHAPSO), N-dodecyl-N,N-(dimethylammonio)butyrate (DDMAB), DDMAU, N-Dodecyl-N,N-dimethylglycine (EMPIGEN BB), Lauryldimethylamine N-oxide (LDAO), n-Octyl-N,N-dimethyl-3-ammonio-1-propanesulfonate, n-Decyl-N,N-dimethyl-3-ammonio-1-propanesulfonate, n-Dodecyl-N,N-dimethyl-3-ammonio-1-propanesulfonate, n-Tetrtadecyl-N,N-dimethyl-3-ammonio-1-propanesulfonate, n-Hexadecyl-N,N-dimethyl-3-ammonio-1-propanesulfonate, n-Octadecyl-N,N-dimethyl-3-ammonio-1-propanesulfonate, 3-(Dodecyldimethylammonio)propanesulfonate, 3-(N,N-Dimethylpalmitylammonio)propanesulfonate, and amidosulfobetaines such as ASB-14, ASB-16 (both from CALBIOCHEM, La Jolla, Calif.). Some synthetic zwitterionic detergents are also known as sulfobetaines.

The non-detergent sulfobetaines, or NDSBs, are typically unable to aggregate and thus do not form micelles. NDSBs typically have a short hydrophobic group and a sulfobetaine hydrophilic group, while zwitterionic detergents typically have a quaternary ammonium ion and a sulfonate group, often with zero net charge. Exemplary non-detergent sulfobetaines include NDSB-195, NDSB-201, NDSB-211, NDSB-221, NDSB-256, and the like. Descriptions of detergents and their use can be found in, among other places, Bhairi, A Guide to the Properties and Uses of Detergents In Biology and Biochemistry, Calbiochem-Novabiochem Corp. (2001); CALBIOCHEM General Catalog 2002-2003; Hjelmeland, Proc. Nat'l. Acad. Sci. USA, 77(11):6368-70 (1980); and Neugebauer, Methods Enzymol. 182:239-53 (1990).

The term "filtration medium" is used broadly herein and refers to any substance or composition that blocks the passage of certain components or particles from a liquid, typically based on size. Filtration media can be porous, including without limitation, filter paper, glass fiber, polymer mesh such as a nylon mesh, a porous disk, or cellulose, and at least some of the sample suspension or enriched culture media can pass through the pores while particles larger than the pore size (including mesh size, where applicable) can not typically pass through. In some embodiments, filtration media are non-porous, for example but not limited to sand, glass beads, diatomaceous earth, gravel, or crushed rock such as perlite including without limitation expanded perlite, and at least some of the enriched culture media can percolate around the individual particles of the filtration media. Some non-limiting examples of filtration media include sheets or layers comprising paper, glass fibers, including without limitation glass wool, quartz fibers, nylon mesh, and textiles, including without limitation woven or knit cloth for example but not limited to burlap, sackcloth, and gauze, including without limitation surgical gauze and cheesecloth; organic polymers such as polysulfone, polyethersulfone, polyacrylonitrile, polyvinyl chloride, polypropylene, polycarbonate, nylon, cellulose acetate; and fluoropolymers, including without limitation polytetrafluoroethylene (PTFE), expanded PTFE (ePTFE), and PTFE composites; granular and/or particulate materials for example but not limited to sand, gravel, perlite, glass beads, diatomaceous earth, crushed glass, agarose beads, and gel-filtration resins, including without limitation carbohydrate polymers, such as cellulose, dextran, or agarose, including cross-linked versions of any of these, such as Sepharose, Sephacel, Sephacryl, and Sephadex. The size, shape and/or composition of a filtration medium is typically not limiting, provided that a selected filtration medium serves the desired purpose. In certain embodiments, a filtration medium is selected to allow at least some of the microorganisms in an enriched medium to pass through, while retaining at least some of the food particles and other particulate matter. In some embodiments, a filtration medium is selected to impede the passage of at least some of the microorganisms, while allowing liquids to pass through. In certain such embodiments, a physical or chemical interaction may occur between the microorganism and the filter. In some embodiments, the microorganism is retained or captured on the filter because the microorganism is larger in diameter than the filter's pore size.

In some embodiments, at least some microorganisms are retained on the filtration medium based on a charge interaction between the microorganisms and the filtration medium. In some embodiments, a filtration medium is hydrophilic or hydrophobic. In some embodiments, the filtration medium is positively charge to enhance capture of negatively charged microorganisms. In some embodiments, a filtration medium is uncharged (neutral charge) to enhance recovery of microorganisms retained on the filter by vortexing or centrifuging the filtration medium in a small volume of buffer or growth medium. In some embodiments, a filtration medium is durable under pressures up to about 900 mm Hg, including without limitation vacuum, gaseous pressure, and hydraulic pressures. In certain embodiments, a filtration medium does not irreversibly absorb, or minimally absorbs, oligonucleotides, enzymes, and other components useful for fluorescent detection. In some embodiments, a filtration membrane shows no or minimal autofluorescence when illuminated with light with a wavelength between 500 and 660 nm. In some embodiments, a filtration medium is wetable in aqueous solutions. In some embodiments, a filtration medium does not substantially inhibit nucleic acid amplification, including primer extension, when present in the amplification mixture, for example but not limited to a PCR reaction mix. In some embodiments, a filtration medium is of relatively uniform thickness to allow reasonably even flow across the filter to generate a comparatively even distribution of microorganisms across the surface of the filtration medium.

Those in the art will appreciate that the selection of filtration medium depends, at least in part, on the composition of the sample, the enriched culture medium, and the microorganisms of interest, i.e., those being evaluated. Those in the art will also appreciate that a variety of filtration membranes are commercially available in a wide range of pore sizes and that, informed by the current teachings and the size and surface properties of the microorganism, one or more could be used effectively as a filtration medium. Some non-limiting examples of commercially available filtration membranes include nylon mesh filters in standard pore sizes of 11, 20, 30, 41, 60, 80, 100, 120, 140, 160, and 180 microns (Millipore); polycarbonate membranes with standard pore sizes of 2, 3, 5, 8, 10, or 12 microns (Whatman, Inc., Florham Park, N.J.); cellulose filters in standard pore size ranges of 20-25, 25-30, and 30-35 microns (Whatman); and Durapore membranes, variously comprising hydrophilic PDVF, mixed cellulose esters/hydrophilic PDVF, or hydrophilic polyethersulfone, and available in standard pore sizes of 0.1, 0.2, 0.22, 0.45, 0.5, or 1.2 microns (Millipore).

The term "microorganism" is used in a broad sense herein and includes cells, tissues and organs from plants and animals, including but not limited to, stem cells, CHO, Vero, Hela, cultured animal cells, and so on, genetically modified plants, non-cellular and unicellular organisms, such as eubacteria, including without limitation cyanobacteria; archaea; protozoa; fungi, including but not limited to, algae and yeast; and certain viruses. Some non-limiting examples of microorganisms include yeast, *Mycoplasma, Escherichia coli*, for example but not limited to enterovirulent strains (such as ETEC, EPEC, O157:H7 or EHEC, and EIEC); *Staphylococcus* species, including but not limited to *S. aureus; Streptococcus* species; *Campylobacter* species, including without limitation *C. jejuni* and *C. coli; Salmonella* species, including without limitation *S. enterica; Vibrio* species, including but not limited to *V. cholerae, V. parahaemolyticus,* and *V. vulnificans; Shigella* species, *Giardia lamblia, Cryptosporidium* species including but not limited to *C. parvum* and *C. muris; Bacillus* species, including but not limited to *B. anthracis* and *B. cereus; Brucella* species; *Yersinia* species including without limitation, *Y. enterocolitica, Y. pseudotuberculosis* and *Y. pestis; Aeromonas* species including without limitation *A. hydrophila; Plesiomonas shigelloides; Entamoeba histolytica; Clostridium botulinum; Listeria* species, including without limitation *L. monocytogenes; Anisakis* species and related worms; *Ascaris lumbricoides; Trichuris trichiura*; and viruses, including without limitation rotavirus, Norwalk virus, hepatitis E virus, hepatitis C virus, vesivirus and mouse minute virus.

In certain embodiments, the microorganisms to be detected are present in a food sample being evaluated, such as meat, fish, fruit, vegetables, beer, wine, eggs, or milk; and including processed forms of any of these, for example but not limited to: processed meats, for example but not limited to, ground meat, luncheon meat, sausages, and canned meat products; fruit or vegetable juice, jam, jelly, or preserves; canned fruits and vegetables; egg products, including without limitation dehydrated eggs; and dairy products such as cheese, cottage cheese, butter, sour cream, and cheese curd. Typically a portion of food or beverage is combined with an appropriate liquid, including without limitation water, a buffer solution, or a culture medium, including without limitation, a selective medium or an enrichment medium. In some embodiments, the food is chopped, macerated, liquefied, diced, or homogenized. In some embodiments, large volumes of sample, for example but not limited to, volumes of 100 mL, 250 mL, or more are processed according to the disclosed methods to determine whether a particular microorganism is present in the starting material. According to certain embodiments, a portion of the food or beverage and appropriate liquid are typically combined to form a dilute suspension, for example but not limited to, ratios of about 1:5, 1:10, or 1:20 (w/vol). In some embodiments, a detergent, an emulsifying agent, or both, is added to enhance the solubility of high lipid foods, for example but not limited to butter and certain other dairy products. Those in the art will appreciate that the choice of liquid used to suspend the food or beverage will depend, at least in part, on the starting material (i.e., the food or beverage) and the microorganism(s) of interest; and that the food/beverage to liquid ratio can vary widely, provided that the suspension is sufficiently fluid to process, for example but not limited to, passing it through a filtration media. In certain embodiments, 25 grams of a solid or semi-solid food is combined with 225 mL of a suitable culture media. In some embodiments, 25 mL of a beverage or a liquefied or partially liquefied food is combined with 225 mL of a suitable culture media.

In certain embodiments, the microorganisms to be detected are present in pharmaceutical products, personal care products, dairy products or in samples of plant, animal, human or environmental origin. Microorganisms may also be detected, if present in raw materials, equipment, products or processes used to manufacture or store food, beverages, water, pharmaceutical products, personal care products dairy products or environmental samples, in clinical specimens, equipment, fixtures or products used to treat humans or animals as well as in clinical samples and clinical environments.

Those of skill in the art will appreciate that detection of microorganism contamination is a concern for both food and health safety. Further, the retesting or destruction of contaminated materials such as food, beverages, water, agricultural products, environmental areas and biopharmaceutical and pharmaceutical products involves major financial losses for the producer or manufacturer. Applications of microbial detection include diagnostic research, biopharmaceutical development, genetic analysis, and environmental testing. Users in these areas would benefit from a discriminatory positive control that would provide the user with confirmation of nucleic acid extraction from the test sample, confirmation of the integrity of the positive control and as an inhibition control to monitor the fidelity of the final, post-extraction sample in the amplification reaction and detection process. Users in these areas must be assured of reproducibility from sample-to-sample, run-to-run, lab-to-lab, and instrument-to-instrument. Traditional methods for detecting food pathogens and microbial contaminants can be very tedious, and may include time-consuming enrichment steps in selective growth media (e.g. 12-36 hours or more), thus it often takes several days before results are obtained. Because of the highly infectious nature of certain microorganisms, the seriousness of the resulting diseases and the limited shelf-life and perishability issues with certain foodstuffs, among other things, there is a continuing need for methods and devices to expedite microbial concentration and detection. There is also a need for methods and kits to rapidly detect microorganisms of interest in environmental samples, including without limitation, samples obtained from a potential bioterror environment. There is also a need for methods and kits to rapidly detect microbial contaminants rapidly and conclusively when performing quality control and quality assurance assays during biopharmaceutical and pharmaceutical manufacturing. There is a need for the assessment and verification of nucleic acid recovery and confidence in a negative sample result during the assessment of pharmaceutical manufacturing steps. Accordingly, in certain embodiments, methods and compositions provided herein are of use in biopharmaceutical or bioproduction workflows in the production of biologic agents and pharmaceuticals. In some embodiments, the methods are incorporated into a biopharmaceutical or bioproduction manufacturing, quality control and/or quality assurance workflows.

As used herein, the term "target polynucleotide" refers to a polynucleotide sequence that is sought to be amplified. The target polynucleotide can be obtained from any source, and can comprise any number of different compositional components. For example, the target can be nucleic acid (e.g. DNA or RNA), and transfer RNA, as well as messenger RNA (mRNA) and/or micro RNA (miRNA). The target can be methylated, non-methylated, or both. Further, it will be appreciated that "target polynucleotide" can refer to the target polynucleotide itself, as well as surrogates thereof, for example amplification products, and native sequences. In some embodiments, the target polynucleotide is a short DNA molecule derived from a degraded source, such as can be found in for example but not limited to forensics samples (see for example Butler, 2001, Forensic DNA Typing: Biology and Technology Behind STR Markers). The target polynucleotides of the present teachings can be derived from any of a number of sources, including without limitation, viruses, prokaryotes, eukaryotes, for example but not limited to plants, fungi, and animals. These sources may include, but are not limited to, whole blood, a tissue biopsy, lymph, bone marrow, amniotic fluid, hair, skin, semen, biowarfare agents, anal secretions, vaginal secretions, perspiration, saliva, buccal swabs, various environmental samples (for example, agricultural, water, and soil), research samples generally, purified samples generally, cultured cells, and lysed cells. It will be appreciated that target polynucleotides can be isolated from samples using any of a variety of procedures known in the art, for example the PrepSEQ™ Kits (from Applied Biosystems), Boom et al., U.S. Pat. No. 5,234,809, MirVana™ RNA isolation kit (Ambion), etc. It will be appreciated that target polynucleotides can be cut or sheared prior to analysis, including the use of such procedures as mechanical force, sonication, restriction endonuclease cleavage, or any method known in the art. In general, the target polynucleotides of the present teachings will be single stranded, though in some embodiments the target polynucleotide can be double stranded, and a single strand can result from denaturation.

The terms "nucleic acid" and "nucleic acid sequence" as used herein, refer to a polymer of ribonucleosides or deoxyribonucleosides that are covalently bonded, typically by phosphodiester linkages between nucleotide subunits. Non-limiting examples of nucleic acids include genomic DNA (gDNA); hnRNA; mRNA; noncoding RNA (ncRNA), including but not limited to rRNA, tRNA, miRNA (micro RNA), siRNA (small interfering RNA), snoRNA (small nucleolar RNA), snRNA (small nuclear RNA) and stRNA (small temporal RNA); fragmented nucleic acid; nucleic acid obtained from subcellular organelles such as mitochondria or chloroplasts; and amplification products comprising nucleotides. Nucleic acids may be naturally-occurring or they may be synthetic. Discussions of nucleic acids may be found in, among other places, Current Protocols in Nucleic Acid Chemistry, S. Beaucage, D. Bergstrom, G. Glick, and R. Jones, eds., John Wiley & Sons, including updates through September 2005 (hereinafter "Beaucage et al."); S. Verma and F. Eckstein, Ann. Rev. Biochem., 67:99-134 (1998); S. Buckingham, Horizon Symposia, Understanding the RNAissance, Nature Publishing Group, May 2003 at pages 1-3; S. Eddy, Nature Rev. Genetics 2:919-29 (2001); and Nucleic Acids in Chemistry and Biology, 2d ed., G. Blackburn and M. Gait, eds., Oxford University Press (1996; hereinafter "Blackburn and Gait").

The term "nucleic acid dye" or "intercalating dye" as used herein refers to a fluorescent molecule that is specific for a double-stranded polynucleotide or that at least shows a substantially greater fluorescent enhancement when associated with a double-stranded polynucleotide than with a single-stranded polynucleotide. Typically nucleic acid dye molecules associate with double-stranded segments of polynucleotides by intercalating between the base pairs of the double-stranded segment, by binding in the major or minor grooves of the double-stranded segment, or both. Non-limiting examples of nucleic acid dyes include ethidium bromide, DAPI, Hoechst derivatives including without limitation Hoechst 33258 and Hoechst 33342, intercalators comprising a lanthanide chelate (for example but not limited to a nalthalene diimide derivative carrying two fluorescent tetradentate β-diketone-Eu3+ chelates (NDI-(BHHCT-$Eu^{3+}$)$_2$), see, e.g., Nojima et al., Nucl. Acids Res. Supplement No. 1, 105-06 (2001)), ethidium bromide, and certain unsymmetrical cyanine dyes such as SYBR® Green, PicoGreen®, and BOXTO.

An "unsymmetrical cyanine dye", sometimes described in the art as an asymmetric cyanine dye or an asymmetrical cyanine dye, refers to a dye molecule with the general formula $R_2N[CH=CH]_nCH=NR_2$, where n is a small number and the R groups typically comprise at least one benzazole group and at least one quinoline group or at least one pyridine group. Non-limiting examples of unsymmetrical cyanine dyes include [2-[N-(3-dimethylaminopropyl)-N-propylamino]-4-[2,3-dihydro-3-methyl-(benzo-1,3-thiazol-2-yl)-methylidene]-1-phenyl-quinolinium] (SYBR® Green), [2-[N-bis-(3-dimethylaminopropyl)-amino)-amino]-4-[2,3-dihydro-3-methyl-(benzo-1,3-thiazol-2-yl)-methylidene]-1-phenyl-quinolinium] (PicoGreen®), 4-[(3-methyl-6-(benzothiazol-2-yl)-2,3-dihydro-(benzo-1,3-thiazole)-2-methylidene)]-1-methyl-pyridinium iodide (BEBO), BOXTO, and BETO. Descriptions of unsymmetrical cyanine dyes can be found in, among other places, Karlsson et al., Nucl. Acids Res. 31:6227-34 (2003); Zipper et al., Nucl. Acids Res. 32:e103 (2004); Bengtsson et al., Nucl. Acids Res. 31:e45 (2003); and Goransson et al., Asymettric cyanine dyes, DNA-Technology 2005, Chalmers University Technology (2005).

The term "reporter probe" refers to a sequence of nucleotides, nucleotide analogs, or nucleotides and nucleotide analogs, that specifically anneals with a corresponding amplicon, for example but not limited to a PCR product, and when detected, including but not limited to a change in intensity or of emitted wavelength, is used to identify and/or quantify the corresponding amplicon or target polynucleotide. Thus, by indirectly detecting the amplicon, one can determine that the corresponding microorganism is present in the sample. Most reporter probes can be categorized based on their mode of action, for example but not limited to: nuclease probes, including without limitation TaqMan® probes; extension probes including without limitation scorpion primers, Lux™ primers, Amplifluors, and the like; and hybridization probes including without limitation molecular beacons, Eclipse probes, light-up probes, pairs of singly-labeled reporter probes, hybridization probe pairs, and the like. In certain embodiments, reporter probes comprise an amide bond, an LNA, a universal base, or combinations thereof, and include stem-loop and stem-less reporter probe configurations. Certain reporter probes are singly-labeled, while other reporter probes are doubly-labeled. Dual probe systems that comprise FRET between adjacently hybridized probes are within the intended scope of the term reporter probe. In certain embodiments, a reporter probe comprises a fluorescent reporter group and a quencher (including without limitation dark quenchers and fluorescent quenchers). Some non-limiting examples of reporter probes include TaqMan® probes; Scorpion probes (also referred to as scorpion primers); Lux™ primers; FRET primers; Eclipse probes; molecular beacons, including but not limited to FRET-based molecular beacons, multicolor molecular beacons, aptamer beacons, PNA beacons, and antibody beacons; labeled PNA clamps, labeled PNA openers, labeled LNA probes, and probes comprising nanocrystals, metallic nanoparticles and similar hybrid probes (see, e.g., Dubertret et al., Nature Biotech. 19:365-70, 2001; Zelphati et al., BioTechniques 28:304-15, 2000). In certain embodiments, reporter probes further comprise minor groove binders including but not limited to TaqMan® MGB probes and TaqMan® MGB-NFQ probes (both from Applied Biosystems). In certain embodiments, reporter probe detection comprises fluorescence polarization detection (see, e.g., Simeonov and Nikiforov, Nucl. Acids Res. 30:e91, 2002).

The term "DNA polymerase" is used in a broad sense herein and refers to any polypeptide that is able to catalyze the addition of deoxyribonucleotides or analogs of deoxyribonucleotides to a nucleic acid polymer in a template dependent manner. For example but not limited to, the sequential addition of deoxyribonucleotides to the 3'-end of a primer that is annealed to a nucleic acid template during a primer extension reaction. Typically DNA polymerases include DNA-dependent DNA polymerases and RNA-dependent DNA polymerases, including reverse transcriptases. Certain reverse transcriptases possess DNA-dependent DNA polymerase activity under certain reaction conditions, including AMV reverse transcriptase and MMLV reverse transcriptase. Such reverse transcriptases with DNA-dependent DNA polymerase activity may be suitable for use with the disclosed methods and are expressly within the contemplation of the current teachings. Descriptions of DNA polymerases can be found in, among other places, Lehninger Principles of Biochemistry, 3d ed., Nelson and Cox, Worth Publishing, New York, N.Y., 2000, particularly Chapters 26 and 29; Twyman, Advanced Molecular Biology: A Concise Reference, Bios Scientific Publishers, New York, N.Y., 1999; Ausubel et al., Current Protocols in Molecular Biology, John Wiley & Sons, Inc., including supplements through May 2005 (hereinafter "Ausubel et al."); Lin and Jaysena, J. Mol. Biol. 271:100-11, 1997; Pavlov et al., Trends in Biotechnol. 22:253-60, 2004; and Enzymatic Resource Guide: Polymerases, 1998, Promega, Madison, Wis. Expressly within the intended scope of the term DNA polymerase are enzymatically active mutants or variants thereof, including enzymes modified to confer different temperature-sensitive properties (see, e.g., U.S. Pat. Nos. 5,773,258; 5,677,152; and 6,183,998; and DNA Amplification: Current Techniques and Applications, Demidov and Broude, eds., Horizon Bioscience, 2004, particularly in Chapter 1.1).

The term "RNA polymerase" is used in a broad sense herein and refers to any polypeptide that is able to catalyze the addition of ribonucleotides or analogs of ribonucleotides to a nucleic acid polymer in a template dependent manner. The RNA polymerase may be, for example, a T bacteriophage RNA polymerase or an SP6 RNA polymerase.

In some embodiments, a primer comprises a "promoter sequence", including without limitation a sequence suitable for binding a T3 RNA polymerase, T7 RNA polymerase, or SP6 RNA polymerase. In some embodiments, a promoter sequence comprises a multiplicity of different sequences suitable for binding an RNA polymerase, for example but not limited to a first sequence suitable for binding a first RNA polymerase and a second sequence suitable for binding a second RNA polymerase. Those in the art understand that as an amplification product is amplified by certain amplification means, the complement of the promoter sequence is synthesized in the complementary amplicon. Thus, it is to be understood that the complement of a promoter sequence is expressly included within the intended meaning of the term promoter sequence, as used herein.

As used herein, "forward" and "reverse" are used to indicate relative orientation of primers on a polynucleotide sequence. For illustration purposes but not as a limitation, consider a single-stranded polynucleotide drawn in a horizontal, left to right orientation with its 5'-end on the left. The "reverse" primer is designed to anneal with the downstream primer-binding site at or near the "3'-end" of this illustrative polynucleotide in a 5' to 3' orientation, right to left. The corresponding "forward primer is designed to anneal with the complement of the upstream primer-binding site at or near the "5'-end" of the polynucleotide in a 5' to 3' "forward" orientation, left to right. Thus, the reverse primer comprises a sequence that is complementary to the reverse or downstream primer-binding site of the polynucleotide and the forward primer comprises a sequence that is the same as the forward or upstream primer-binding site. It is to be understood that the terms "3-end" and "5'-end" as used in this paragraph are illustrative only and do not necessarily refer literally to the respective ends of the polynucleotide. Rather, the only limitation is that the reverse primer of this exemplary primer pair anneals with a reverse primer-binding site that is downstream or to the right of the forward primer-binding site that comprises the same sequence as the corresponding forward primer. As will be recognized by those of skill in the art, these terms are not intended to be limiting, but rather to provide illustrative orientation in a given embodiment.

Multi-element interacting detectors are also within the intended scope of the term detector, such as fluorophore-quencher pairs, including without limitation fluorescent quenchers and dark quenchers (also known as non-fluorescent quenchers). A fluorescent quencher can absorb the fluorescent signal emitted from a fluorophore and after absorbing enough fluorescent energy, the fluorescent quencher can emit fluorescence at a characteristic wavelength, e.g., fluorescent resonance energy transfer (FRET). For example without limitation, the FAM-TAMRA pair can be illuminated at 492 nm, the excitation peak for FAM, and emit fluorescence at 580 nm, the emission peak for TAMRA. A dark quencher, appropriately paired with a fluorescent reporter group, absorbs the fluorescent energy from the fluorophore, but does not itself fluoresce. Rather, the dark quencher dissipates the absorbed energy, typically as heat. Some non-limiting examples of dark or nonfluorescent quenchers include Dabcyl, Black Hole Quenchers, Iowa Black, QSY-7, AbsoluteQuencher, Eclipse non-fluorescent quencher, metal clusters such as gold nanoparticles, and the like. Certain dual-labeled probes comprising fluorophore-quencher pairs can emit fluorescence when the members of the pair are physically separated, for example but without limitation, nuclease probes such as TaqMan® probes. Other dual-labeled probes comprising fluorophore-quencher pairs can emit fluorescence when the members of the pair are spatially separated, for example but not limited to hybridization probes such as molecular beacons or extension probes such as Scorpion primers. Fluorophore-quencher pairs are well known in the art and used extensively for a variety of probes (see, e.g., Yeung et al., BioTechniques 36:266-75, 2004; Dubertret et al., Nat. Biotech. 19:365-70, 2001; and Tyagi et al., Nat. Biotech. 18:1191-96, 2000).

The terms "target region" and "microbial target region" refer to a segment of a microbial nucleic acid that is being amplified and analyzed to determine the presence or absence of the microorganism in the starting material. The target region is generally located between two flanking sequences, a first target flanking region and a second target flanking region, located on either side of, but not necessarily immediately adjacent to, the target region. In some embodiments, a nucleic acid segment comprises a plurality of different target regions. In some embodiments, a target region is contiguous with or adjacent to one or more different target regions. In some embodiments, a given target region can overlap a first target region on its 5'-end, a second target region on its 3'-end, or both.

A target region can be either synthetic or naturally occurring. Certain target regions, including flanking sequences where appropriate, can be synthesized using oligonucleotide synthesis methods that are well-known in the art. Detailed descriptions of such techniques can be found in, among other places, Beaucage et al.; and Blackburn and Gait. Automated DNA synthesizers useful for synthesizing target regions, primers, and probes are commercially available from numerous sources, including for example, the Applied Biosystems DNA Synthesizer Models 381A, 391, 392, and 394 (Applied Biosystems, Foster City, Calif.). Target regions, including flanking regions where appropriate, can also be generated biosynthetically, using in vivo methodologies and/or in vitro methodologies that are well known in the art. Descriptions of such technologies can be found in, among other places, Sambrook et al., Molecular Cloning, A Laboratory Manual, Cold Spring Harbor Press (1989) (hereinafter "Sambrook et al."); and Ausubel et al. Nucleic acid can also be obtained from biological materials using any suitable sample preparation technique known in the art. Purified or partially purified nucleic acid is commercially available from numerous sources, including Coriell Cell Repositories, Coriell Institute for Medical Research, Camden, N.J.; Serologicals Corp., Norcross, Ga.; Stratagene, La Jolla, Calif.; and the American Type Culture Collection (ATCC), Manassas, Va.

The term "discriminating positive control" as used herein refers to a nucleic acid sequence added to a sample being assayed to assess for example, but not limited to, extraction of nucleic acid from the sample, presence of inhibitors precluding nucleic acid detection in the sample, and/or confirm detection of a target nucleic acid sequence in a test sample. The discriminating positive control provides confirmation as seen as a positive result when assaying for the extraction of nucleic acid, the method for the detection of the presence of nucleic acid or the fidelity of the reaction method for the detection of the presence of nucleic acid. The discriminating positive control shares the same primer-binding sites of the microorganism of interest. However, unlike the microorganism of interest, the discriminating positive control can be differentiated from the nucleic acid sequence of the microorganism of interest in that it differs in its nucleic acid sequence, amplicon sequence, melting temperature ($T_m$) and melt curve. Because the positive result for the discriminating positive control is distinguishable from a positive result for the microorganism of interest, the concern of a false positive is removed and fidelity of results is ensured.

In certain embodiments, the discriminating positive control nucleic acid molecule is at least 15 nucleotides in length. In some embodiments, the discriminating positive control nucleic acid molecule is at least 20, at least 30, at least 40, at least 50, at least 60, at least 70, at least 80, at least 90 or at least 100 nucleotides in length. In certain embodiments, the discriminating positive control nucleic acid molecule is less than 3000 nucleotides in length. In some embodiments, the discriminating positive control nucleic acid molecule is less than 2000, less than 1000, less than 500, less than 400, less than 300, less than 200, less than 150, less than 100, less than 80 nucleotides in length. In certain embodiments, the discriminating positive control nucleic acid molecule is about 20 to 3000 nucleotides in length. In some embodiments, the discriminating positive control nucleic acid molecule is about 20 to 500, about 20 to 200, about 30 to 200, about 40 to 150, about 40 to 120, about 40 to 100 nucleotides in length.

In certain embodiments, the $T_m$ of the discriminating positive control nucleic acid, or an amplicon thereof, is at least 1° C. higher or lower than the $T_m$ of the corresponding microorganism target nucleic acid, or amplicon thereof. In some embodiments, the $T_m$ of the discriminating positive control nucleic acid, or an amplicon thereof, is at least 2° C. higher or lower than the $T_m$ of the corresponding microorganism target nucleic acid, or amplicon thereof. In some embodiments, the $T_m$ of the discriminating positive control nucleic acid, or an amplicon thereof, is at least 3° C. higher or lower than the $T_m$ of the corresponding microorganism target nucleic acid, or amplicon thereof. In some embodiments, the difference of the $T_m$ of the discriminating positive control nucleic acid from that of the $T_m$ of the corresponding microorganism target nucleic acid is 2° C., 3° C., 4° C. or 5° C. In some embodiments, the $T_m$ of the discriminating positive control nucleic acid, or an amplicon thereof, is about 2° C. higher than the $T_m$ of the corresponding microorganism target nucleic acid, or amplicon thereof. In some embodiments, the $T_m$ of the discriminating positive control nucleic acid, or an amplicon thereof, is about 3° C. higher than the $T_m$ of the corresponding microorganism target nucleic acid, or amplicon thereof. In some embodiments, the $T_m$ of the discriminating positive control nucleic acid, or an amplicon thereof, is about 4° C. higher than the $T_m$ of the corresponding microorganism target nucleic acid, or amplicon thereof.

In some embodiments, the discriminating positive control is added prior to extraction of nucleic acid from the test sample which can contain the microorganism of interest to verify the extraction of nucleic acid from the test sample including, if present, extraction of the microorganism of interest as well as the method of extraction. In some embodiments, the discriminating positive control is added to control water, i.e., nucleic acid free water, to serve as a positive control of the reactants for a polymerase chain reaction. In some embodiments, the discriminating positive control is added prior to amplification of the nucleic acid of the microorganism of interest to verify the fidelity of the amplification reaction and rule out inhibitors of the amplification reaction. Inhibitors can be from the extraction reaction or components of the amplification reaction can be inactive, of the wrong concentration, degraded, or inadvertently omitted from the amplification reaction.

The term "primer" refers to a polynucleotide that selectively hybridizes to a target region flanking sequence or to a corresponding primer-binding site of an amplification product; and allows the synthesis of a sequence complementary to the corresponding polynucleotide template from its 3' end.

The terms "microbe-specific primer pair" and "microorganism-specific primer pair" as used herein, refer to two corresponding primers, comprising a forward target-specific primer and a reverse target-specific primer, that are designed to amplify a particular microbial target region that is generally diagnostic for the microorganism of interest. The forward target-specific primer comprises a first target-specific portion that comprises a sequence that is the same as or substantially the same as the nucleotide sequence of the first or upstream target flanking sequence, and that is designed to selectively hybridize with the complement of the upstream target flanking sequence that is present in, among other places, the opposite strand of a double-stranded target region or reverse amplification product. In some embodiments, the forward target-specific primer further comprises a first tail portion, located upstream from the first target-specific portion that comprises a first primer-binding site. The reverse target-specific primer of the primer pair comprises a second target region-specific portion that comprises a sequence that is complementary to, and that is designed to selectively hybridize with, the second or downstream target region flanking sequence. In some embodiments, the reverse target-specific primer further comprises a second tail portion, located upstream from the second target-specific portion that comprises a second primer-binding site. In certain embodiments, at least one forward target-specific primer, at least one reverse target-specific primer, or at least one forward target-specific primer and at least one reverse target-specific primer further comprises at least one of: a reporter probe-binding site, an additional primer-binding site, and a reporter group, for example but not limited to a fluorescent reporter group.

According to the instant teachings, microbial nucleic acid may be extracted from any microorganism, including a prokaryote, an archaea, or certain eukaryotes. Certain viral genomic DNA or genomic RNA is also within the scope of the current teachings. In certain embodiments, the nucleic acid may be present in a double-stranded or single-stranded form. The skilled artisan appreciates that genomic nucleic acid includes not only full length material, but also fragments generated by any number of means, for example but not limited to, enzyme digestion, sonication, shear force, and the like, and that all such material, whether full length or fragmented, represent forms of nucleic acid that can serve as templates for an amplifying reaction of the current teachings.

The terms "amplifying" and "amplification" are used in a broad sense and refer to any technique by which a target region, an amplicon, or at least part of an amplicon, is reproduced or copied (including the synthesis of a complementary strand), typically in a template-dependent manner, including a broad range of techniques for amplifying nucleic acid sequences, either linearly or exponentially. Some non-limiting examples of amplification techniques include primer extension, including the polymerase chain reaction (PCR), RT-PCR, asynchronous PCR (A-PCR), and asymmetric PCR, strand displacement amplification (SDA), multiple displacement amplification (MDA), nucleic acid strand-based amplification (NASBA), rolling circle amplification (RCA), transcription-mediated amplification (TMA), and the like, including multiplex versions, or combinations thereof. Descriptions of certain amplification techniques can be found in, among other places, Molecular Cloning, A Laboratory Manual, Cold Spring Harbor Press, 3d ed., 2001 (hereinafter "Sambrook and Russell"); Sambrook et al.; Ausubel et al.; PCR Primer: A Laboratory Manual, Diffenbach, Ed., Cold Spring Harbor Press (1995); Msuih et al., J. Clin. Micro. 34:501-07 (1996); PCR: A Practical Approach, McPherson et al. (eds.) IRL Press, Oxford; The Nucleic Acid Protocols Handbook, Rapley, ed., Humana Press, Totowa, N.J. (2002); U.S. Pat. Nos. 6,027,998 and 6,511,810; PCT Publication Nos. WO 97/31256 and WO 01/92579; Ehrlich et al., Science 252:1643-50 (1991); Favis et al., Nature Biotechnology 18:561-64 (2000); Protocols & Applications Guide, rev. 9/04, Promega, Madison, Wis.; and Rabenau et al., Infection 28:97-102 (2000).

The terms "amplification product" and "amplicon" are essentially used interchangeably herein and refer to the nucleic acid sequences generated from any cycle of amplification of any amplification reaction. An amplicon can be either double-stranded or single-stranded, including the separated component strands obtained from a double-stranded amplification product.

In certain embodiments, amplification techniques comprise at least one cycle of amplification, for example, but not limited to, the steps of: denaturing double-stranded nucleic acid; selectively hybridizing a primer to a target region flanking sequence or a primer-binding site of an amplicon (or complements of either, as appropriate); and synthesizing a strand of nucleotides in a template-dependent manner using a polymerase. The cycle may or may not be repeated.

Amplification can comprise thermocycling or can be performed isothermally. In some embodiments, amplifying comprises a thermocycler, for example but not limited to a GeneAmp® PCR System 9700, 9600, 2700, 2400 thermalcyclers, a StepOne™, or a StepOne Plus™ real-time PCR systems, the Applied Biosystems 7300 Real-Time PCR System, the Applied Biosystems 7500 Real-Time PCR System, and the Applied Biosystems 7900 HT Fast Real-Time PCR System (all from Applied Biosystems). In some embodiments, double-stranded amplification products are not initially denatured, but are used in their double-stranded form in one or more subsequent steps. In certain embodiments, single-stranded amplicons are generated in an amplification reaction, for example but not limited to asymmetric PCR or A-PCR.

Primer extension according to the present teachings is an amplification process comprising elongating a primer that is annealed to a template in the 5' to 3' direction using a template-dependent polymerase. According to certain embodiments, with appropriate buffers, salts, pH, temperature, and appropriate dNTPs, a template-dependent polymerase incorporates nucleotides complementary to the template strand starting at the 3'-end of an annealed primer, to generate a complementary strand. In certain embodiments, the polymerase used for primer extension lacks or substantially lacks 5'-exonuclease activity, 3'-exonuclease activity, or both. Descriptions of certain primer extension reactions can be found in, among other places, Sambrook et al., Sambrook and Russell, and Ausubel et al.

In certain embodiments, an amplification reaction comprises multiplex amplification, in which a multiplicity of different target regions, a multiplicity of different amplification product species, or both, are simultaneously amplified using a multiplicity of different primer pairs (see, e.g., Henegariu et al., BioTechniques 23:504-11, 1997; and Rapley, particularly in Chapter 79). Certain embodiments of the disclosed methods comprise a multiplex amplification reaction and a single-plex amplification reaction, including a multiplicity of single-plex reactions performed in parallel.

In some embodiments, amplification comprises a two-step PCR reaction including without limitation a pre-amplification step wherein a limited number of cycles of amplification occur (for example but not limited to 2 to about 15 cycles of amplification), then the resulting amplicon is typically diluted and portions of the diluted amplicon are subjected to additional cycles of amplification in a subsequent amplification step (see, e.g., Marmaro and Gordes, U.S. Pat. No. 6,605,451; and Andersen and Ruff, U.S. Pat. Application Publication No. US 2004/0175733).

In certain embodiments, an amplifying reaction comprises asymmetric PCR. According to certain embodiments, asymmetric PCR comprises an amplification composition comprising (i) at least one primer pair in which there is an excess of one primer, relative to the corresponding primer of the primer pair, for example but not limited to a five-fold, a ten-fold, or a twenty-fold excess; (ii) at least one primer pair that comprises only a forward primer or only a reverse primer; (iii) at least one primer pair that, during given amplification conditions, comprises a primer that results in amplification of one strand and a corresponding primer that is disabled; or (iv) at least one primer pair that meets the description of both (i) and (iii) above. Consequently, when a target region or an amplification product is amplified, an excess of one strand of the subsequent amplification product (relative to its complement) is generated. Descriptions of asymmetric PCR, can be found in, among other places, McPherson, particularly in Chapter 5; and Rapley, particularly in Chapter 64.

In some embodiments, the methods of the current teachings comprise Q-PCR. The term "quantitative PCR", or "Q-PCR" refers to a variety of methods used to quantify the results of the polymerase chain reaction for specific nucleic acid sequences. Such methods typically are categorized as kinetics-based systems, that generally determine or compare the amplification factor, such as determining the threshold cycle (CO, or as co-amplification methods, that generally compare the amount of product generated from simultaneous amplification of target and standard templates. Many Q-PCR techniques comprise reporter probes, intercalating agents, or both. For example but not limited to TaqMan® probes (Applied Biosystems), i-probes, molecular beacons, Eclipse probes, scorpion primers, Lux™ primers, FRET primers, ethidium bromide, SYBR® Green I (Molecular Probes), and PicoGreen® (Molecular Probes).

Certain methods of optimizing amplification reactions are known to those skilled in the art. For example, it is known that PCR may be optimized by altering times and temperatures for annealing, polymerization, and denaturing, as well as changing the buffers, salts, and other reagents in the reaction composition. Optimization may also be affected by the design of the primers used. For example, the length of the primers, as well as the G-C:A-T ratio may alter the efficiency of primer annealing, thus altering the amplification reaction. Descriptions of amplification optimization can be found in, among other places, James G. Wetmur, "Nucleic Acid Hybrids, Formation and Structure," in Molecular Biology and Biotechnology, pp. 605-8, (Robert A. Meyers ed., 1995); McPherson, particularly in Chapter 4; Rapley; and Protocols & Applications Guide, rev. 9/04, Promega.

Certain amplification compositions comprise dUTP and uracil-N-glucosidase (UNG). Discussion of use of dUTP and UNG may be found, for example, in Kwok et al., Nature, 339:237-238, 1989; and Longo et al., Gene, 93:125-128, 1990.

In some embodiments, an amplification reaction is followed by a "clean-up" or "purifying" step, wherein at least some of the components of the amplification reaction composition are removed from at least some of the amplicons, thereby purifying the amplicons. Purifying typically comprises a degrading means, including an enzyme such as a nuclease or a phosphatase, or a separating means, including a physical separation means such as a spin column or a separation based on hybridization, such as hybridization-based pullout. For example but not limited to, degrading and/or separating at least some of the unincorporated primers, unincorporated NTPs, enzymes including a polymerase, salts, other amplification composition components, or combinations thereof. In some embodiments, purifying an amplification product comprises a "spin column" or other centrifugal or gel-based separation means; a degradation reaction comprising for example an exonuclease, a phosphatase, or both (e.g., ExoSAP-It® reagent. USB Corp. Cleveland, Ohio), or an exonuclease and an apyrase; a hybridization-based separation means; or a precipitation step, for example but not limited to, ethanol precipitation in the presence of a salt, such as sodium or potassium acetate.

Those in the art will appreciate that in certain embodiments, purifying an amplification product can, among other things, decrease the amount of primers needed in a subsequent amplification reaction, decrease possible side reactions, and/or reduce competition due to unincorporated primers and/or dNTPs from a previous amplification reaction.

The term "degrading" is used in a broad sense herein and refers to any technique in which an unincorporated dNTP or nucleotide analog is rendered unincorporable, typically by enzymatic digestion by a phosphatase; an unincorporated primer is digested, typically by an nuclease; or both.

In some embodiments, purifying comprises a nuclease, such as a DNase, for example but not limited to exonuclease I, mung bean nuclease, S1 nuclease, exonuclease T, or combinations thereof. In some embodiments, a dNTP and/or an unincorporated primer is degraded. In some embodiments, unincorporated dNTPs are degraded using an apyrase or a phosphatase, including shrimp alkaline phosphatase (SAP) or calf intestinal phosphatase (CIP). In some embodiments, degrading unincorporated primers and unincorporated dNTPs comprises an apyrase, an inorganic pyrophosphate (PPi), and an exonuclease. Those in the art will appreciate that the method for degrading unincorporated primers and/or unincorporated dNTPs is typically not limiting, provided that the desired polynucleotides, typically amplification products, are not degraded or at least not substantially degraded, while the unincorporated primers and dNTPs are degraded.

In some embodiments, unincorporated primers, unincorporated dNTPs, amplification composition reagents, or combinations thereof, are separated from an amplification product by, for example but not limited to, gel or column purification, sedimentation, filtration, beads, including streptavidin-coated beads, magnetic separation, or hybridization-based pull out, including annealing amplification products comprising hybridization tags to a solid support. A number of kits and reagents for performing such separation techniques are commercially available, including the Wizard® MagneSil™ PCR Clean-Up System (Promega), the MinElute PCR Purification Kit, the QIAquick Gel Extraction Kit, the QIAquick Nucleotide Removal Kit, the QIAquick 96 PCR Purification Kit or BioRobot Kit (all from Qiagen, Valencia, Calif.), Dynabeads® (Dynal Biotech LLC), or the ABI PRISM® Duplex™ 384 Well F/R Sequence Capture Kit (Applied Biosystems P/N 4308082). In some embodiments, an amplification product is not purified prior to a subsequent amplifying reaction.

The term "concentrating" as used herein refers to a process in which the relative quantity of microorganisms in a sample (per unit volume or area) is increased compared to the relative quantity of microorganisms in the sample before the concentration step, excluding an increase in numbers due to growth of the microorganism. According to certain embodiments of the present teachings, microorganisms are concentrated on the surface or in the pores of certain filter media, for example but not limited to, a 0.45 µm or a 0.22 µm filter. In other embodiments, microorganisms are concentrated on a surface comprising a binding partner, including without limitation, an antibody or binding protein/peptide, for example but not limited to a magnetic or paramagnetic bead or particle coated with an antibody specific for the microorganism to be detected. In certain such embodiments, the concentrating further comprises a magnetic field. In some embodiments, microorganisms are concentrated using centrifugation, absorption, adsorption, or combinations thereof. In some embodiments, concentrating comprises a magnetic field, including without limitation an electromagnetic field. Those in the art understand that the concentration techniques in the disclosed employed are generally not limiting. Rather, a wide variety of means for concentrating microorganisms are within the scope of the disclosed methods and kits The terms "detecting" and "detection" are used in a broad sense herein and encompass any technique by which one can determine whether or not a particular microorganism, i.e., a microorganism of interest, is present in a sample. In some embodiments, the presence of a surrogate is detected, directly or indirectly, allowing the presence or absence of a microorganism to be determined. For example but not limited to, detecting a family of labeled sequencing products obtained using a microbial amplicon as the template; detecting the fluorescence generated when a nuclease reporter probe, annealed to an amplification product, is cleaved by a polymerase; or detecting the $T_m$ when the fluorescence is no longer detectable due to separation of the strands of the double-stranded amplicon, wherein the detectable signal; detectable change in signal; or differences in $T_m$ indicates that the corresponding microbial target sequence has been amplified and thus the microorganism is present in the sample. In some embodiments, detecting comprises quantitating the detectable signal, including without limitation, a real-time detection method, such as quantitative PCR ("Q-PCR"). In some embodiments, detecting comprises determining the sequence of a sequencing product or a family of sequencing products generated using an amplification product as the template; in some embodiments, such detecting comprises obtaining the sequence of a family of sequencing products.

In certain embodiments, detecting comprises an instrument, i.e., using an automated or semi-automated detecting means that can, but need not, comprise a computer algorithm. In certain embodiments, a detecting instrument comprises or is coupled to a device for graphically displaying the intensity of an observed or measured parameter of an extension product or its surrogate on a graph, monitor, electronic screen, magnetic media, scanner print-out, or other two- or three-dimensional display and/or recording the observed or measured parameter. In certain embodiments, the detecting step is combined with or is a continuation of at least one separating step, for example but not limited to a capillary electrophoresis instrument comprising at least one fluorescent scanner and at least one graphing, recording, or readout component; a chromatography column coupled with an absorbance monitor or fluorescence scanner and a graph recorder; a chromatography column coupled with a mass spectrometer comprising a recording and/or a detection component; or a microarray with a data recording device such as a scanner or CCD camera. In certain embodiments, the detecting step is combined with an amplifying step, for example but not limited to, real-time analysis such as Q-PCR. In certain embodiments, the detecting step is combined with an amplifying step, for example but not limited to, a melt curve determination. Exemplary means for performing a detecting step include the ABI PRISM® Genetic Analyzer instrument series, the ABI PRISM® DNA Analyzer instrument series, the ABI PRISM® Sequence Detection Systems instrument series, and the Applied Biosystems Real-Time PCR instrument series (all from Applied Biosystems); and microarrays and related software such as the Applied Biosystems microarray and Applied Biosystems 1700 Chemiluminescent Microarray Analyzer and other commercially available microarray and analysis systems available from Affymetrix, Agilent, and Amersham Biosciences, among others (see also Gerry et al., J. Mol. Biol. 292:251-62, 1999; De Bellis et al., Minerva Biotec 14:247-52, 2002; and Stears et al., Nat. Med. 9:140-45, including supplements, 2003) or bead array platforms (Illumina, San Diego, Calif.). Exemplary software includes GeneMapper™ Software, GeneScan® Analysis Software, Genotyper® Software, and RapidFinder™ Software (all from Applied Biosystems).

In certain embodiments, an amplification product can be detected and quantified based on the mass-to-charge ratio of at least a part of the amplicon (m/z). For example, in some embodiments, a primer comprises a mass spectrometry-compatible reporter group, including without limitation, mass tags, charge tags, cleavable portions, or isotopes that are incorporated into an amplification product and can be used for mass spectrometer detection (see, e.g., Haff and Smirnov, Nucl. Acids Res. 25:3749-50, 1997; and Sauer et al., Nucl. Acids Res. 31:e63, 2003). An amplification product can be detected by mass spectrometry allowing the presence or absence of the microorganism to be determined. In some embodiments, a primer comprises a restriction enzyme site, a cleavable portion, or the like, to facilitate release of a part of an amplification product for detection. In certain embodiments, a multiplicity of amplification products are separated by liquid chromatography or capillary electrophoresis, subjected to ESI or to MALDI, and detected by mass spectrometry. Descriptions of mass spectrometry can be found in, among other places, The Expanding Role of Mass Spectrometry in Biotechnology, Gary Siuzdak, MCC Press, 2003.

In certain embodiments, surrogates such as a reporter probe or a cleaved portion of a reporter probe are detected, directly or indirectly. For example but not limited to, hybridizing an amplification product to a labeled reporter probe comprising a quencher, including without limitation, a molecular beacon, including stem-loop and stem-free beacons, a TaqMan® probe or other nuclease probe, a Light-Speed™ PNA probe, or a microarray capture probe. In certain embodiments, the hybridization occurs when the molecular beacon and the amplification product are free in solution and a detectable signal or a detectably different signal is emitted. In other embodiments, an amplification product hybridizes to or is bound to a solid surface such as a microarray and a detectable signal or a detectably different signal is emitted (see, e.g., EviArrays™ and EviProbes™, Evident Technologies).

In certain embodiments, detecting comprises measuring or quantifying the detectable signal of a reporter group or the change in a detectable signal of a reporter group, typically due to the presence of an amplification product. For illustration purposes but not as a limitation, an unhybridized reporter probe may emit a low level, but detectable signal that quantitatively increases when hybridized with the amplification product, including without limitation, certain molecular beacons, LNA probes, PNA probes, and light-up probes (see, e.g., Svanik et al., Analyt. Biochem. 281:26-35, 2000; Nikiforov and Jeong, Analyt. Biochem. 275:248-53, 1999; and Simeonov and Nikiforov, Nucl. Acids Res. 30:e91, 2002). In certain embodiments, detecting comprises measuring fluorescence polarization.

In certain embodiments, detecting comprises measuring or quantifying the detectable signal of a fluorescent dye which intercalates (binds) to the amplification product of a test sample or a control sample, typically double-stranded DNA, and emits a fluorescent signal in response to light. Detection follows the amplification phase in which the temperature of the sample is increased until the double-stranded DNA denatures into two single strands resulting in release of the dye and lowering of the signal. A melt curve can then be determined by plotting the change in fluorescence verse temperature. An exemplary melt curve is shown in FIG. 1. The apex of the curve is the temperature at which the double stranded amplicon is still double-stranded, giving off the greatest fluorescent signal and the decrease in fluorescence is indicated by a drop in fluorescence signal as the double-stranded nucleic acid disassociates into two single strands.

In some embodiments, determining whether a particular microorganism is present in a sample comprises evaluating an internal standard or a control sequence, such as a standard curve for the corresponding target region, an internal size standard, or combinations thereof. In some embodiments, a control sequence or an internal reference dye is employed to account for lane-to-lane, capillary-to-capillary, and/or assay-to-assay variability. In certain embodiments, an internal control sequence comprises an unrelated nucleic acid that is extracted in parallel or added to the test sample before extraction of the sample's nucleic acid to confirm extraction of nucleic acid. In some embodiments, an internal control sequence comprises an unrelated nucleic acid that is amplified in parallel following the extraction of nucleic acid to validate the amplification reaction was not inhibited by reactants of the extraction process. In certain embodiments, an internal control sequence comprises an unrelated nucleic acid that is amplified in parallel to validate the amplification reaction or the detection technique.

In some embodiments, detecting comprises a manual or visual readout or evaluation, or combinations thereof. In some embodiments, detecting comprises an automated or semi-automated digital or analog readout. In some embodiments, detecting comprises real-time or endpoint analysis. In some embodiments, detecting comprises a microfluidic device, including without limitation, a TaqMan® Low Density Array (Applied Biosystems). In some embodiments, detecting comprises a real-time detection instrument. Exemplary real-time instruments include, the ABI PRISM® 7000 Sequence Detection System, the ABI PRISM® 7700 Sequence Detection System, the Applied Biosystems 7300 Real-Time PCR System, the Applied Biosystems 7500 Real-Time PCR System, the Applied Biosystems 7900 HT Fast Real-Time PCR System (all from Applied Biosystems); the LightCycler™ System (Roche Molecular); the Mx3000P™ Real-Time PCR System, the Mx3005P™ Real-Time PCR System, and the Mx4000® Multiplex Quantitative PCR System (Stratagene, La Jolla, Calif.); and the Smart Cycler System (Cepheid, distributed by Fisher Scientific). Descriptions of real-time instruments can be found in, among other places, their respective manufacturer's users manuals; McPherson; DNA Amplification: Current Technologies and Applications, Demidov and Broude, eds., Horizon Bioscience, 2004; and U.S. Pat. No. 6,814,934.

Those in the art understand that the detection techniques employed are generally not limiting. Rather, a wide variety of detection means are within the scope of the disclosed methods and kits, provided that they allow the presence or absence of a microorganism in the sample to be determined.

In some embodiments, the methods of the current teachings are performed before, after, or in conjunction with a sequencing reaction. The term "sequencing" is used in a broad sense herein and refers to any technique known in the art that allows the order of at least some consecutive nucleotides in at least part of a polynucleotide to be identified. Some non-limiting examples of sequencing techniques include Sanger's dideoxy terminator method and the chemical cleavage method of Maxam and Gilbert, including variations of those methods; sequencing by hybridization; and restriction mapping. Some sequencing methods comprise electrophoreses, including capillary electrophoresis and gel electrophoresis; sequencing by hybridization including microarray hybridization; mass spectrometry; and single molecule detection. In some embodiments, sequencing comprises direct sequencing, duplex sequencing, cycle sequencing, single base extension sequencing (SBE), solid-phase sequencing, or combinations thereof. In some embodiments, sequencing comprises detecting the sequencing product using an instrument, for example but not limited to an ABI PRISM® 377 DNA Sequencer, an ABI PRISM® 310, 3100, 3100-Avant, 3730, or 3730xl Genetic Analyzer, an ABI PRISM® 3700 DNA Analyzer (all from Applied Biosystems), or a mass spectrometer. In some embodiments, sequencing comprises incorporating a dNTP, including a dATP, a dCTP, a dGTP, a dTTP, a dUTP, a dITP, or combinations thereof and including dideoxyribonucleotide versions of dNTPs, into an amplification product.

Those in the art will appreciate that the sequencing method employed is not typically a limitation of the present methods. Rather any sequencing technique that provides the order of at least some consecutive nucleotides of at least part of the corresponding amplification product can typically be used with the current methods. Descriptions of sequencing techniques can be found in, among other places, McPherson, particularly in Chapter 5; Sambrook and Russell; Ausubel et al.; Siuzdak, The Expanding Role of Mass Spectrometry in Biotechnology, MCC Press, 2003, particularly in Chapter 7; and Rapley.

In some embodiments, the disclosed methods and kits comprise a microfluidics device, "lab on a chip", or micrototal analytical system (μTAS). In some embodiments, an amplification reaction is performed using a microfluidics device. In some embodiments, a Q-PCR reaction is performed using a microfluidic device. In certain embodiments, an amplification product is detected in a microfluidic device. In some embodiments, a sequencing reaction is performed and the nucleotide sequence of at least a part of an amplification product is obtained using a microfluidics device. Descriptions of exemplary microfluidic devices can be found in, among other places, Published PCT Application Nos. WO/0185341 and WO 04/011666; Kartalov and Quake, Nucl. Acids Res. 32:2873-79, 2004; and Fiorini and Chiu, BioTechniques 38:429-46, 2005.

According to the current teachings, methods for the rapid detection of a microorganism or a group of microorganisms in a sample, for example but not limited to a food, water, environmental, agricultural, biopharmaceutical, or pharmaceutical sample, are provided. At least a portion of the starting material is combined with a culture medium or streaked onto a culture plate that is typically selected to facilitate the growth of the microorganism being evaluated. For illustration purposes but not as a limitation, one may combine 25 milliliters (mL) of a liquid food sample or 25 grams (g) of a solid or semisolid food sample with 225 mL enrichment broth to form an inoculated medium. The medium is incubated for a few hours, typically between about four hours and about eleven hours or twelve hours or less, including all intervening time points in those ranges as if each were expressly listed herein, to allow the microorganisms in the medium to propagate. The incubation temperature varies depending on the growth requirements of the microorganism of interest, but typically is in the range of 35° C. to 42° C., including all intervening temperatures in that range as if each were expressly listed herein. The atmospheric oxygen tension varies depending on the growth requirements of the microorganism of interest and can include without limitation atmospheric oxygen tensions that are considered aerobic, anaerobic, or microaerophilic. According to certain methods, the inoculated medium is mixed by stirring or agitation during at least part of the incubation period. Alternatively, a sample may be tested without prior enrichment such as when testing for *Mycoplasma* contamination in cell culture. At least some of the microorganisms are concentrated and the microbial nucleic acid is extracted. Nucleic acid extraction can be accomplished using the PrepSEQ™ Sample Preparation Kits (from Applied Biosystems).

Depending on the starting sample and the composition of the enriched medium, it may be passed through a filtration medium before it is centrifuged to remove at least some of the particulate in the solution. In some embodiments, the enriched medium is allowed to sit undisturbed for a period of time at the end of the incubation period to allow large particles to settle out of the incubated medium. In certain embodiments, a portion of the settled medium is decanted or withdrawn from the top of the settled medium and centrifuged. Typically, as much of the settled medium as is reasonably possible is obtained while minimizing the transfer of the debris that has settled to the bottom of the reaction vessel.

According to certain methods, after the inoculated medium has been incubated, typically for about 4 hours to about 8 hours or at least twelve hours or less, it is passed through at least one and typically a series of filters and at least some of the enriched microorganisms are captured. For example but not as a limitation, the enriched medium is passed through a filtration medium comprising a large pore, for example but not limited to a 5 micron filter and the first filtrate is passed through a second filtration medium comprising a smaller pore size, for example but not limited to a 0.45 micron filter. In some embodiments, the second filtrate is passed though yet another filtration medium with an even smaller pore size, for example but not limited to a 0.22 micron filter or a 0.20 micron filter. Typically at least some of the microorganisms are captured or trapped on or in the final filtration medium, for example but not limited to, a 0.45 micron filter or a 0.2 micron filter. In some embodiments, the filtration medium comprising the captured microorganisms, typically a membrane filter, is combined with a suitable solution (for example but not limited to nutrient broth or an appropriate buffer) in a suitable reaction vessel (for example but without limitation, 20 mL of culture medium in as a 50 mL plastic tube). The reaction vessel is vigorously agitated or vortexed to release or dislodge at least some of the microorganisms. The filtration medium is typically removed from the tube and the solution comprising the released microorganisms is centrifuged to pellet the microorganisms. In some embodiments, a suitable carrier or co-precipitant is added to the solution comprising the dislodged microorganisms prior to the centrifugation step. After centrifugation, the supernatant is removed and the pellet comprising the microorganisms is resuspended in a solution, typically a hypotonic solution such as nuclease-free distilled water or a low osmotic strength buffer.

In some embodiments, the concentrated microorganisms are resuspended in a liquid, for example but not limited to, an appropriate buffer or isotonic solution, and combined with a solid support comprising affinity binding moieties. For example but not as a limitation, beads comprising specific antibodies or binding partners such as peptides or recombinant proteins that can bind to a particular microorganism. Provided that the solid support comprises a suitable binding partner, at least some of the microorganisms are bound to the solid support. The unbound material is removed, typically the support is washed, then the support is exposed to a solution, typically a hypotonic solution including without limitation nuclease-free distilled water, generally in a very small volume, for example but not limited to 5-25 microliters.

According to certain methods, extracting the microbial nucleic acid comprises lysing a microbial cell using an enzymatic means, a chemical means, a physical means, or combinations thereof. Non-limiting examples of enzymatic means for lysing microbial cells include proteolytic enzymes such as lysozyme, protease, including without limitation pronase and proteinase K, lysostaphin, liabase, lyticase, and mutanolysin. Non-limiting examples of chemical means for lysing microbial cells include mucolytic agents, for example but not limited to, N-acetylcysteine; detergents; alkaline lysis; and drying agents including without limitation acetone and certain alcohols including ethanol, isopropanol, and phenol. Non-limiting examples of physical means for lysing microbial cells include heat, for example but not limited to, boiling; freeze-thaw treatments; sonication; electrical treatment, including without limitation electrolysis; pressure treatment, including without limitation, a French press, a grinding means such as a mortar and pestle, grinding with beads or solid particles for example but not limited to glass beads, sand, fine gravel, and carborundum, a bead-beater, or a homogenizer; osmotic shock; shearing, for example but not limited to extruding the microorganism through a narrow opening for example but not limited to a fine gauge hypodermic needle or a micro-capillary; and drying, for example but not limited to, lyophilization and dehydration.

In some embodiments, extracting the microbial nucleic acid comprises resuspending the concentrated microorganisms in a solution comprising a detergent, an emulsifying agent, or combinations thereof, and the microbial nucleic acid is isolated. In some embodiments, extracting comprises using a commercially available reagent or kit, including without limitation PrepMan Ultra® Sample Preparation Reagent (Applied Biosystems) or the High Pure foodproof II Kit (Roche Applied Science).

The extracted microbial nucleic acid is amplified and detected. In certain embodiments, the microbial nucleic acid is combined with a DNA polymerase, a microbe-specific primer pair for each microorganism of interest, and optionally a reporter probe. In some embodiments, at least some of the extracted nucleic acid is contacted with at least one primer, typically a primer pair specific for a target region that is diagnostic for the microorganism of interest. Under suitable conditions, at least one target-specific primer anneals with the extracted nucleic acid and the target region is amplified by a DNA polymerase. In some embodiments, a primer comprises a promoter sequence that becomes incorporated into the amplification product. In certain such embodiments, the amplification product is combined with an RNA polymerase and the amplification product is further amplified. In some embodiments, the amplifying comprises a multiplicity of different microbe-specific primer pairs, with at least one microbe-specific primer pair for each microorganism being evaluated.

Provided herein, in certain embodiments, is a reaction mixture comprising a test sample, a discriminating positive control nucleic acid molecule, a microorganism-specific primer pair, a polymerase and at least one detectable reporter. In other embodiments, the reaction mixture comprises an extract of a test sample, a discriminating positive control nucleic acid molecule, a microorganism-specific primer pair, a polymerase and at least one detectable reporter.

In some embodiments comprising end-point detection, after the microbial target regions are amplified, the amplification product, the complement of an amplification product, a surrogate for an amplification product, or combinations thereof are detected, directly or indirectly, and the presence or absence of the corresponding microorganism is determined. In certain embodiments comprising real-time detection, while the microbial target regions and amplicons are being amplified, an amplification product, the complement of an amplification product, a surrogate for an amplification product, or combinations thereof are detected, directly or indirectly, and the presence or absence of the corresponding microorganism is determined. In some embodiments, detecting comprises a different reporter probe for each microorganism to be evaluated. In certain embodiments, detecting comprises a nucleic acid dye.

The instant teachings also provide kits designed to expedite performing the subject methods. Kits serve to expedite the performance of the methods of interest by assembling two or more components required for carrying out the methods. Kits preferably contain components in pre-measured unit amounts to minimize the need for measurements by end-users. Kits preferably include instructions for performing one or more of the disclosed methods. Preferably, the kit components are optimized to operate in conjunction with one another.

Certain kit embodiments comprise a microorganism-specific primer, typically a microorganism-specific primer pair; a DNA polymerase, including without limitation, a reverse transcriptase, a DNA-dependent DNA polymerase, or both; a discriminating positive control nucleic acid sequence, a nucleic acid dye; and at least one of: a filtration medium; a solid support comprising a affinity binding moiety, including without limitation a magnetic bead or a paramagnetic bead comprising an antibody or a peptide binding partner; a surfactant, for example but not limited to, a detergent, a emulsifying agent, or both; a carrier or co-precipitant; a reporter probe, a positive control plasmid DNA; and a hypotonic solution.

The current teachings, having been described above, may be better understood by reference to examples. The following examples are intended for illustration purposes only, and should not be construed as limiting the scope of the teachings herein in any way.

EXAMPLES

Example 1: Determining the Presence or Absence of a Microorganism in a Solid Food Sample Twenty-five grams of a ground beef sample are added to a filtered stomacher bag (e.g., a 15 cm×23 cm filtered Whirl-Pak® bag, #B01348WA, Nasco, Fort Atkinson, Wis.) and the weight adjusted to 250 g using brain heart infusion broth (BHI) as the culture medium. The inoculated medium is homogenized using a stomacher laboratory blender (e.g., GSR Technical Sales, Edmonton, AB, Canada; or AGB Scientific Ltd., Dublin, Ireland) for about 60 seconds at normal speed. The stomacher bag is incubated at 37° C. on a rotating table set at about 125 rpm to enrich the microorganisms of interest. The incubation time and temperatures vary depending on the specific microorganism of interest and the type of sample. For illustration purposes but not as a limitation, about five hours for a milk or ground meat sample being evaluated for *E. coli*; about five and a half hours for a milk sample or about six hours for a ground meat sample being evaluated for *Salmonella enterica*; or about eleven hours for a milk sample and about twelve hours for a ground meat sample being evaluated for *Listeria monocytogenes*. Those in the art understand that the incubation times and temperatures will vary depending on, among other things, the doubling time of the particular microorganism, the culture medium employed, the incubation conditions, and the sample, but that appropriate incubation times and conditions can be determined using methods known in the art and in light of the current teachings.

Five grams of perlite (e.g., Harborlite Corp., #Harborlite 1500) is added to a stomacher bag without a filter partition. A filtration unit is prepared by placing a 47 mm diameter filter with a pore size of eleven µm (e.g., Nylon Net Filter, #NY11 047 00, Millipore Corp.) in a vacuum filtration unit (e.g., a Sterifil Aseptic Systems for 47 mm disc filters, Millipore). The incubated culture comprising the ground meat is poured from the side of the filtered stomacher bag that does not comprise the largest ground meat fragments into the stomacher bag comprising the perlite or other suitable filtration medium. The bag is closed and the incubated medium and the filtration medium are mixed together by shaking. The contents are filtered through the 11 µm filter using vacuum filtration. The perlite forms a cake over the membrane during filtration. After the liquid has passed through the filter, an additional 25 mL of nutrient broth is added to the perlite filter cake and filtered through under vacuum. The combined filtrate is centrifuged in a centrifuge, e.g., a Beckman Alegra 25R, for 15 minutes at 8,000 rpm. The supernatant is decanted and the centrifuge bottles are inverted to drain the residual supernatant. Excess fat is removed, if necessary, with a piece of sterile gauze (e.g., ITW Texwipe, # TX708A). The pellets in the drained centrifuged bottles are resuspended in about 1.2 mL phosphate buffered saline (PBS) and transferred to a 1.5 mL microcentrifuge tube. The tube is centrifuged in a bench-top microcentrifuge for three minutes at maximum speed and the resulting supernatant is removed. To extract the microbial nucleic acid, the pellet is resuspended in 200 µL PrepMan™ Ultra Sample Preparation Reagent (Applied Biosystems) and between 10 µL and 50 µL of discriminatory positive control is added and the tube incubated at 95° C. for ten minutes, then cooled for two minutes at room temperature. The cooled microfuge tube is transferred to an Eppendorf microfuge and centrifuged at maximum speed for three minutes. A ten µL aliquot of the supernatant comprising the microbial nucleic acid is diluted by mixing with 90 µL nuclease-free distilled water. A 10 µL aliquot of discriminatory positive control is added to a separate tube containing 90 µL nuclease-free distilled water to confirm amplification reactants and conditions. The nucleic acid is amplified and detected by combining 10 µL of the diluted PrepMan solution to which in a amplification reaction composition comprising a microbe-specific primer pair for each microorganism being evaluated and in parallel a separate amplification reaction is run containing a 5 µL aliquot of discriminatory positive control to confirm no inhibitors of the amplification reaction exist in the diluted PrepMan solution. The nucleic acid is amplified and detected by combining 10 µL of the diluted PrepMan solution in an amplification reaction composition comprising a microbe-specific primer pair for each microorganism being evaluated an appropriate TaqMan® reporter probe and PCR master mix, in a final volume of 25 µL. An internal positive control sequence (TaqMan® Exogenous IPC Reagent, P/N 4308323, Applied Biosystems) and a passive reference dye are included in the amplification reaction composition. The extracted nucleic acid is amplified by PCR and the cleaved reporter probe detected using an Applied Biosystems 7500 Real-Time PCR System and the associated software. The discriminatory positive control nucleic acid is amplified using the same microbe-specific primer pair and TaqMan® reporter probe as used by at least one of the microorganisms being evaluated.

Example 2: Determining the Presence or Absence of a Microorganism in a Liquid Food Sample Twenty-five milliliters (mL) of a milk sample are added to a nonfiltered stomacher bag (e.g., a 15 cm×23 cm Whirl-Pak® bag, #B01196WA, Nasco, Fort Atkinson, Wis.) containing 225 mL brain heart infusion broth (BHI) culture medium. The inoculated medium in the stomacher bag is incubated at 37° C. on a rotating platform set at about 125 rpm for an appropriate time, e.g., 5-6 hours to enrich the microorganisms of interest. The enriched medium is transferred to centrifuge bottles and centrifuged in a Beckman Alegra 25R centrifuge for 15 minutes at 8,000 rpm. The supernatant is decanted and the centrifuge bottles are inverted to drain the residual supernatant. Excess fat is removed with sterile gauze (e.g., ITW Texwipe, # TX708A). The pellets in the drained centrifuged bottles are resuspended in about 1.0 mL PBS, transferred to a 1.5 mL microcentrifuge tube, and 20 µL Dynal Magnetic beads (Dynal Biotech LLC; beads with antibodies that specifically bind *Salmonella, E. coli* 0157:H7, or *Listeria* are commercially available) are added to the 1 mL suspension. The beads are concentrated using a magnet, the supernatant is aspirated, and the beads are washed twice with PBST (PBS containing 0.05% Tween 20), according to the manufacturer's "Manual Method" instructions. The final bead pellet is resuspended in 10 µL nuclease-free distilled water and the entire volume is added to the amplification reaction composition. The nucleic acid in the resuspended pellet is amplified and analyzed as described in Example 1 to determine the presence or absence of the microorganism of interest in the food sample.

Example 3: Determining the Presence or Absence of a Microorganism in a Liquid Food Sample Twenty-five grams of a ground beef sample are added to a filtered stomacher bag (e.g., a 15 cm×23 cm filtered Whirl-Pak® bag, #B01348WA, Nasco, Fort Atkinson, Wis.) and the weight adjusted to 250 g using brain heart infusion broth (BHI) as the culture medium. The inoculated medium is homogenized using a stomacher laboratory blender (e.g., GSR Technical Sales, Edmonton, AB, Canada; or AGB Scientific Ltd., Dublin, Ireland) for about 60 seconds at normal speed. The stomacher bag is incubated at 37° C. on a rotating table set at about 125 rpm to enrich the microorganisms of interest. The enriched medium is first filtered using perlite, as described in example 1. The filtrate is filtered a second time through a 5 micron filter (e.g., a Durapore membrane in a filtration assembly, Millipore Corp.) and the second filtrate is then filtered through a 0.45 micron filter (e.g., a Durapore membrane, Millipore Corp.). The 0.45 micron filter is removed and transferred to a sterile 50 mL polypropylene tube containing 20 mL BHI medium. The tube is vortexed for about three minutes to dislodge the microorganisms from the surface of the membrane filter. The membrane is removed from the tube, ten microliters of GlycoBlue™ (Ambion, Austin Tex.) co-precipitant and between 10 µL and 50 µL of discriminatory positive control is added to the tube to confirm nucleic acid extraction, and the tube is centrifuged at 8,000 rpm for 15 minutes to pellet the microorganisms. The supernatant is aspirated and the pellet is resuspended in 10 µL sterile water. The nucleic acid in the resuspended pellet is amplified and analyzed as described in Example 1 to determine the presence or absence of the microorganism of interest in the food sample.

Example 4: Determining the Presence or Absence of a Microorganism in a Water Sample One liter of a water sample is filtered through a 0.22 micron filter in a filtration assembly. The membrane is transferred to a suitable incubation vessel containing 90 mL of tryptic soy broth and vigorously shaken or vortexed for three minutes to dislodge the bacteria trapped on the surface of the filter. The filter is removed from the incubation vessel and the inoculated medium is incubated for about 6 hours at 37° C. on a rotary shaker at about 80 rpm. The enriched medium is transferred to two sterile 50 mL conical centrifuge tubes, 20 µL of GlycoBlue™ is added to each tube, between 10 µL and 50 µL of discriminatory positive control is added to only one tube and the tubes are centrifuged at 8000 rpm for 15 minutes. The supernatant is aspirated and the pellet is resuspended in 10 µL nuclease-free distilled water. The nucleic acid in the resuspended pellet is amplified and analyzed as described in Example 1 to determine the presence or absence of the microorganism of interest in the water sample.

Example 5: Determining the Presence or Absence of a Microorganism in a Biopharmaceutical or Pharmaceutical Sample by Use of a Nucleic Acid Dye Samples are prepared according to the PrepSEQ™ Ultra Sample Preparation Reagent Protocol (PN 4367554) or the PrepSEQ™ *Mycoplasma* Nucleic Acid Extraction Kit Protocol (PN 4401253) (both from Applied Biosystems). To each labeled tube or reaction well add 18 µL of PreMix solution comprising 15.0 µL Power SYBR® Green PCR Master Mix (2×) and 3.0 µL microbe-specific primer pair mix (10×). For the negative control add 12.0 µL sterile water (negative control); for the inhibition positive control add 2.0-10.0 µL test sample and 2.0 µL discriminatory positive control DNA, adjusting the final volume to 30 µL; for the positive control add 2.0 µL discriminatory positive control DNA and 20 µL sterile water; and for the test sample add 2.0 µL sample and 10.0 µL sterile water. The nucleic acid is amplified by PCR and the SYBR® Green dye signal is detected using an Applied Biosystems Real-Time PCR System with a dissociation curve added after the amplification reaction and the associated software. The discriminatory positive control nucleic acid is amplified using the same microbe-specific primer pair as used to test for the microorganisms being evaluated. PCR conditions, HOLD: 95° C., 10 min., 40 cycles at 95° C., 15 sec, 60° C., followed by dissociation: 95° C., 15 sec. 60° C., 1 min and 95° C., 15 sec. or refer to the instrument's dissociation-curve setup for information on running the dissociation-curve program.

Example 6: Determining the Presence or Absence of a Microorganism in a Solid Food Sample by Use of a Nucleic Acid Dye Follow the sample preparation and extraction method as described in Example 1 and set up the amplification and dissociation reactions as described in Example 5 to determine the presence or absence of the microorganism of interest in the solid food sample.

Example 7: Determining the Presence or Absence of a Microorganism in a Liquid Food Sample by Use of a Nucleic Acid Dye Follow the sample preparation and extraction method as described in Example 2 and set up the amplification and dissociation reactions as described in Example 5 to determine the presence or absence of the microorganism of interest in the liquid food sample.

Example 8: Determining the Presence or Absence of a Microorganism in a Liquid Food Sample by Use of a Nucleic Acid Dye Follow the sample preparation and extraction method as described in Example 3 and set up the amplification and dissociation reactions as described in Example 5 to determine the presence or absence of the microorganism of interest in the liquid food sample.

Example 9: Determining the Presence or Absence of a Microorganism in a Water Sample by Use of a Nucleic Acid Dye Follow the sample preparation and extraction method as described in Example 4 and set up the amplification and dissociation reactions as described in Example 5 to determine the presence or absence of the microorganism of interest in the water sample.

Example 10: Determining the Presence or Absence of a Microorganism in an Environmental Sample by Use of a Nucleic Acid Dye Follow the sample preparation and extraction methods and set up the amplification and dissociation reactions as described in Example 5 to determine the presence or absence of the microorganism of interest in the environmental sample.

Example 11: Determining the Presence or Absence of a Microorganism in an Agricultural Sample by Use of a Nucleic Acid Dye Follow the sample preparation and extraction methods and set up the amplification and dissociation reactions as described in Example 5 to determine the presence or absence of the microorganism of interest in the agricultural sample.

Example 12: Designing a Discriminating Positive Control

The discriminating positive control template (DPC) is a double stranded synthetic DNA molecule consisting of an internal "stuffer" fragment flanked by binding sites for two specific TaqMan® assay primers. The 5' to 3' strand is indicated a "X" and the complementary, 3' to 5' reverse strand is indicated by "Z" in the illustration below. The stuffer fragment is indicated by "SSSS . . . SSS" and the primer-binding sites are underlined "XXXX...XXX" (forward primer, Primer 1) and underlined "ZZZZ...ZZZ" (reverse primer, Primer 2). When included in a TaqMan® assay, the assay primers facilitate amplification of the DPC. In general, the stuffer fragment was between as few as 8 nucleotides in length and up to 40 nucleotides in length, not accounting for the length of the primers flanking the stuffer fragment. Selection of the stuffer fragment was based on high % GC rich regions of the microorganism of interest or of a naturally occurring high % GC genome region but not necessarily polymorphic repeat regions, as would be understood by one of skill in the art. Basing the stuffer fragment on a naturally occurring nucleotide sequence assured that the sequence was easily replicated by DNA polymerase.

Determination of Melting Temperature ($T_m$)

The $T_m$ of the DPC is influenced by the length and nucleotide composition of the DPC sequence. Because DNA melting is a complex reaction that is highly sequence-specific, even subtle changes in the primer binding sites or stuffer nucleotide sequence can have a significant effect on the DPC $T_m$. Additionally, the concentration of monovalent (e.g., $Na^+$) and divalent (e.g., $Mg^{2+}$) cations also effects $T_m$. Each of these cations is found within the TaqMan® reaction mix used in TaqMan® qPCR assays. The $T_m$ prediction algorithm, OligoAnalyzer (Integrated DNA Technologies, Inc. (Coralville, Iowa)), was used to predict the calculated DPC $T_m$, and accounted for cation concentration when calculating $T_m$. Because $T_m$ prediction algorithms have been optimized for short DNA sequences (up to about 25 bp, the length range of typical oligonucleotide primers), the $T_m$ prediction of longer sequences was not as accurate. Therefore, testing of between ten and around thirteen DPCs with the desired $T_m$ value were designed and then tested empirically to determine actual $T_m$ (data not shown).

Designing of the Nucleotide Primer-Binding Site Sequences

In general, the DPC began with the forward primer sequence and ended with the reverse complement of the reverse primer sequence. However, when using more than two amplification primers, the DPC was designed to have only one forward and one reverse primer-binding site. The primer-binding sites were identical to or very close to identical to the primer-binding sites of the microorganism of interest. In order to obtain double stranded amplicons with elevated $T_m$, GC-rich sequences were inserted between the primer binding sites.

Designing of the "Stuffer Fragment" Nucleotide Sequence

The stuffer fragment can be omitted depending upon the $T_m$ of the DPC in relation to the $T_m$ of the amplicon of the microorganism of interest. The minimal DPC had no stuffer, just two primer binding sites. The length of the stuffer fragment was changed to influence the $T_m$. Increasing the length of the stuffer from 8 bp to 30 bp for a pure GC sequence resulted in a 3° C. increase in $T_m$ with an almost linear response. Increasing the length of a pure GC stuffer beyond 30 bp was found to have a negligible effect on $T_m$. When a longer DPC was desired, a GC-rich stuffer of the desired length was inserted between the primer binding sites. If the resulting $T_m$ of the resulting DPC was too high, the $T_m$ was adjusted by changing a fraction of the G and C bases to A and/or T. For a DPC with a 50 bp internal stuffer, the $T_m$ can be modulated over a 2° C. range by changing from 4 to 11 C and G bases to A and/or T.

Cloning of the Discriminating Positive Control

The resulting DPCs selected had a $T_m$ of between 82° C. to 85° C., good PCR efficiency and strong signal level (the derivative seen in the $T_m$ curve, data not shown). The selected DPCs were cloned into a DNA vector and can be subsequently cloned into a larger vector (having a size of around 12 Kb). It is known that plasmid DNA is not recovered as efficiently as higher molecular weight DNA when using the PrepSeq™ Kits. Therefore the DPC can be cloned into, for example but not limited to bacteriophage Lambda (genome size approx. 55 Kb), increasing molecular weight of the DPC. Recovery is only of concern if the assay is quantitative. So long as the nucleic acid of the DPC is recovered and detected in a polymerase chain reaction, it serves as a discriminatory positive control.

Those in the art will appreciate that these illustrative examples are not limiting and that a variety of combinations of suitable culture media, incubation times, concentration methods, including without limitation, different filtration media, nucleic acid extraction procedures, amplification techniques and detection methods can be employed within the scope of the current teachings. Those in the art will understand that the person of ordinary skill, informed by the current teachings, can determine the presence or absence of a microorganism of interest in a wide variety of food samples, water samples, agricultural samples, environmental samples, biopharmaceutical and pharmaceutical samples, or suitable clinical samples, typically in about 12 hours or less and often in a single work day.

The compositions, methods, and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

The foregoing examples are for illustration purposes and are not intended to limit the scope of the teachings herein. Although the disclosed teachings has been described with reference to various applications, methods, compositions, and kits, it will be appreciated that various changes and modifications may be made without departing from the teachings herein. The foregoing examples are provided to better illustrate the present teachings and are not intended to limit the scope of the teachings herein. Certain aspects of the present teachings may be further understood in light of the following claims.

What is claimed is:

1. A method for determining the presence or absence of a microorganism nucleic acid in a test sample, the method comprising:
   (i) preparing a nucleic acid extract of the test sample and making a plurality of portions of the extract;
   (ii) contacting a first portion of the extract with a PCR primer and a double strand intercalating dye;
   (iii) contacting a second portion of the nucleic acid extract with the PCR primer, the double strand intercalating dye, and a discriminatory positive control (DPC) nucleic acid comprising a stuffer fragment and at least one identical or nearly identical PCR primer binding site as the microorganism nucleic acid;
   (iv) amplifying (ii) and (iii), wherein (iii) produces a DPC amplicon and a microorganism amplicon, when present;
   (v) generating melt curves for amplicons of (iv);
   (vi) determining the presence or absence of the microorganism nucleic acid in the test sample, wherein:
      i. the presence of a distinct first peak on the melt curve of step (iii) determines the presence of the DPC nucleic acid, and the absence of a distinct second peak on the melt curve of steps (ii) and (iii) determines the absence of the microorganism nucleic acid in the test sample;
      ii. the presence of the distinct second peak on the melt curve of (ii) and (iii) determines the presence of the microorganism nucleic acid in the test sample.

2. The method of claim 1, wherein the absence of the DPC amplicon indicates that the method is inconclusive.

3. The method of claim 1, wherein the microorganism comprises a bacterium or a virus.

4. The method of claim 1, wherein the test sample comprises an isolated colony, a loopful of cells, an edge of a filamentous colony, a culture broth, an enriched culture broth, a food sample, an environmental sample, an agricultural sample, a biopharmaceutical sample, a pharmaceutical sample, or water.

5. The method of claim 1, wherein the amplifying comprises at least one microorganism-specific primer pair and a polymerase chain reaction (PCR).

6. The method of claim 5, wherein the microorganism nucleic acid comprises a multiplicity of different microorganisms, the microorganism-specific primer pair comprises a multiplicity of different microorganism-specific primer pairs, and the detecting comprises a multiplicity of different amplified nucleic acids.

7. The method of claim 1, wherein the method is part of a biopharmaceutical manufacturing, quality control or quality assurance workflow.

8. A method of minimizing false positive results in a test sample comprising:
   (i) preparing a nucleic acid extract from at least some of the test sample and making a plurality of portions of the nucleic acid extract;
   (ii) contacting a first portion of the extract with a primer, a double strand intercalating dye, and a discriminatory positive control (DPC) nucleic acid comprising a stuffer fragment, and contacting a second portion of the extract with the primer and the double strand intercalating dye, wherein the primer is capable of binding to the DPC nucleic acid when present or to the target nucleic acid when present;
   (iii) amplifying the DPC nucleic acid resulting in a DPC amplicon when present, and, if present, the target nucleic acid resulting in a target amplicon;

(iv) detecting the presence or absence of the target amplicon and detecting the presence or absence of the DPC amplicon,
wherein said detecting comprises measuring a detectable signal of the double strand intercalating dye over a change in temperature; and generating a first melt peak for the DPC amplicon when present, and a second melt peak for the target amplicon if present;
wherein
  i. the presence of the first melt peak of step (iv) determines the presence of the DPC amplicon, and the absence of the second peak on the melt curve of step (iv) determines the absence of the microorganism nucleic acid in the test sample;
  ii. the presence of the second peak on the melt curve of (iv) determines the presence of the microorganism nucleic acid in the test sample.

9. The method of claim 8, wherein the target nucleic acid is viral, prokaryotic or eukaryotic.

10. The method of claim 8, wherein the method is part of a biopharmaceutical manufacturing, quality control or quality assurance workflow.

11. The method of claim 1, wherein a melting temperature of the DPC amplicon is at least 2° C. higher than a melting temperature for the microorganism amplicon.

12. The method of claim 1, wherein a melting temperature of the DPC amplicon is about 2° C. to about 5° C. higher or lower than a melting temperature of the microorganism amplicon.

13. The method of claim 8, wherein a melting temperature of the DPC amplicon is about 2° C. to about 5° C. higher or lower than a melting temperature for the target amplicon.

14. The method of claim 1, wherein a melting temperature for the DPC amplicon is at least 80° C.

15. The method of claim 8, wherein a melting temperature for the DPC amplicon is about 82° C. to about 85° C.

16. The method of claim 8, wherein the presence or absence of the target amplicon in the test sample indicates the presence or absence of the target nucleic acid in the test sample.

17. The method of claim 8, wherein the test sample comprises an isolated colony, a loopful of cells, an edge of a filamentous colony, a culture broth, an enriched culture broth, a food sample, an environmental sample, an agricultural sample, a biopharmaceutical sample, a pharmaceutical sample, or water.

18. The method of claim 8, wherein microorganism nucleic acid comprises a multiplicity of different microorganisms, the microorganism-specific primer pair comprises a multiplicity of different microorganism-specific primer pairs, and the detecting comprises a multiplicity of different amplified nucleic acids.

19. The method of claim 8, wherein a melting temperature for the amplicon of the DPC nucleic acid is at least 80° C.

20. The method according to claim 1 wherein the intercalating dye is selected from the group consisting of ethidium bromide, propidium iodide, DAPI, a Hoechst derivative, an inter-chelator comprising a lanthanide chelate and an unsymmetrical cyanine dye.

21. The method according to claim 20 wherein the unsymmetrical cyanine dye is either a SYBR® Green dye, PicoGreen®, BEBO, BETO or BOXTO.

22. The method according to claim 1 wherein the detectable signal of the intercalating dye is fluorescence and dissociation of a double stranded amplicon is observed by measuring a change in fluorescence.

* * * * *